US008567340B2

(12) United States Patent
Papp et al.

(10) Patent No.: US 8,567,340 B2
(45) Date of Patent: Oct. 29, 2013

(54) SYSTEM AND METHOD FOR COATING A MEDICAL DEVICE

(75) Inventors: John E. Papp, Temecula, CA (US);
Matthew J. Gillick, Murrieta, CA (US);
Kent C. B. Stalker, San Marco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 922 days.

(21) Appl. No.: 12/540,302

(22) Filed: Aug. 12, 2009

(65) Prior Publication Data
US 2011/0039013 A1    Feb. 17, 2011

(51) Int. Cl.
*B05C 5/02* (2006.01)

(52) U.S. Cl.
USPC ............. 118/66; 118/641; 118/642; 118/643; 118/58; 118/64; 118/323

(58) Field of Classification Search
USPC ........................ 118/66, 323, 641–643, 58, 64; 222/222.01, 222.09–222.12; 427/2.1, 427/2.24, 2.29; 34/104
See application file for complete search history.

(56) References Cited

U.S. PATENT DOCUMENTS

| | | |
|---|---|---|
| 4,611,623 A | 9/1986 | Goodrich |
| 5,032,052 A | 7/1991 | Swain |
| 5,090,355 A | 2/1992 | DiMaio et al. |
| 5,209,181 A * | 5/1993 | Flood ............................ 118/322 |
| 5,897,911 A | 4/1999 | Loeffler |
| 6,527,863 B1 | 3/2003 | Pacetti et al. |
| 6,695,923 B1 * | 2/2004 | Schultz et al. ................ 118/679 |
| 7,211,150 B1 | 5/2007 | Kokish et |
| 7,402,329 B2 | 7/2008 | Pacetti et al. |
| 7,404,979 B1 | 7/2008 | Pacetti |
| 8,028,650 B2 * | 10/2011 | Jinbo et al. .................... 118/642 |
| 2002/0041899 A1 | 4/2002 | Chudzik et al. |
| 2003/0106789 A1* | 6/2003 | Schertler .................... 204/192.1 |
| 2004/0194704 A1* | 10/2004 | Chappa et al. ................ 118/719 |
| 2006/0035012 A1 | 2/2006 | Pacetti et al. |
| 2007/0003688 A1 | 1/2007 | Chen et al. |

(Continued)

FOREIGN PATENT DOCUMENTS

| | | |
|---|---|---|
| DE | 100 32 398 | 2/2001 |
| EP | 1 195 584 | 4/2002 |

(Continued)

OTHER PUBLICATIONS

U.S. Appl. No. 10/255,913, filed Sep. 26, 2002, Tang et al.

(Continued)

*Primary Examiner* — Laura Edwards
(74) *Attorney, Agent, or Firm* — Squire Sanders (US) LLP

(57) ABSTRACT

A system and method allows for processing of two groups of medical devices, both groups being alternatingly spray coated within the same enclosure. The two groups repeatedly move back and forth between a spray area and a drying area which is isolated from the spray area. One group moves into the spray area as the other group moves out and into the drying area. Thereafter, the group in the spray area moves out and into the drying area and the other group moves back into the spraying area for a second coating. The alternating process may be repeated any number of times. The spray area may be located inside a sealed spray isolator enclosure and surrounded by gas discharge nozzles.

40 Claims, 20 Drawing Sheets

(56) References Cited

U.S. PATENT DOCUMENTS

Figure 1:
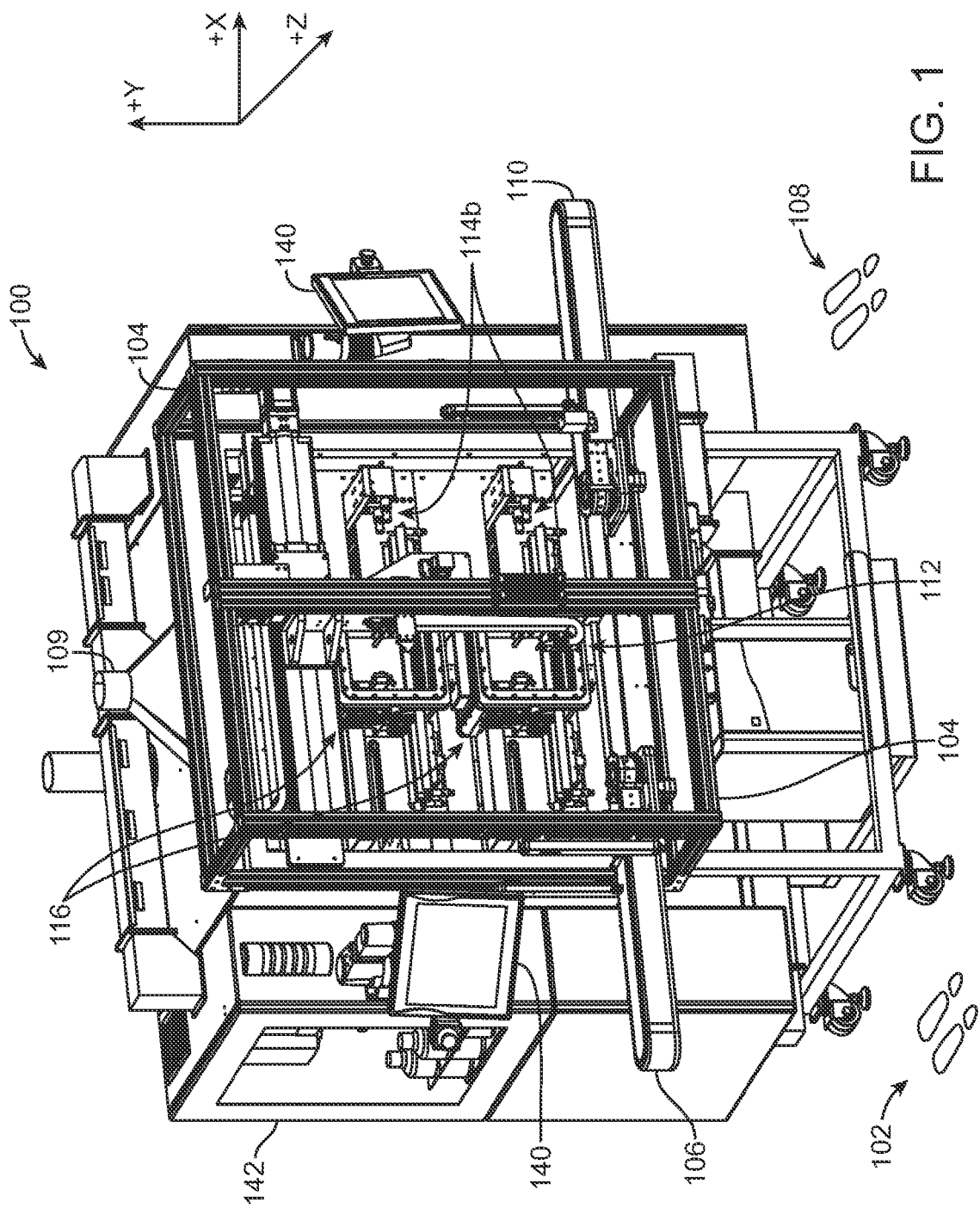

| 2007/0259100 | A1 | 11/2007 | Guerriero et al. |
| 2008/0087474 | A1 | 4/2008 | Nufer et al. |
| 2008/0307668 | A1 | 12/2008 | Van Sciver et al. |
| 2008/0311281 | A1 | 12/2008 | Van Sciver et al. |
| 2008/0312747 | A1 | 12/2008 | Van Sciver et al. |
| 2008/0312869 | A1 | 12/2008 | Van Sciver et al. |

FOREIGN PATENT DOCUMENTS

| GB | 2333476 | 1/1988 |
| JP | 406031227 | 2/1994 |
| WO | WO 2007/130257 | 11/2007 |
| WO | WO 2008/156920 | 12/2008 |
| WO | WO 2009/097448 | 8/2009 |

OTHER PUBLICATIONS

U.S. Appl. No. 10/750,312, filed Dec. 30, 2003, Desnoyer et al.
U.S. Appl. No. 10/805,407, filed Mar. 18, 2004, Yip et al.
U.S. Appl. No. 11/193,849, filed Jul. 28, 2005, Harold et al.
International Search Report and the Written Opinion, for PCT/US2008/061806, mailed Dec. 5, 2008, 19 pgs.
Invitation to pay additional fees, including communication relating to the results of the partial international search, for PCT/US2008/061806, mailed Aug. 27, 2008, 9 pgs.
International Search Report and the Written Opinion, for PCT/US2009/032878, mailed Jun. 19, 2009, 19 pgs.
International Search Report and the Written Opinion, for PCT/US2010/045228, mailed Nov. 22, 2010, 8 pgs.

* cited by examiner

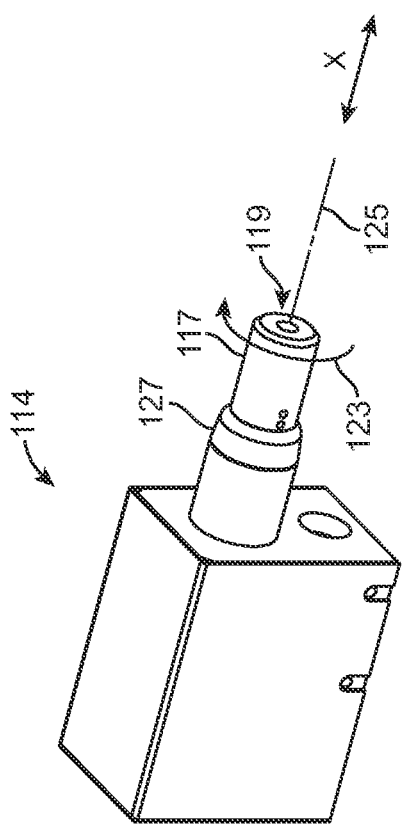
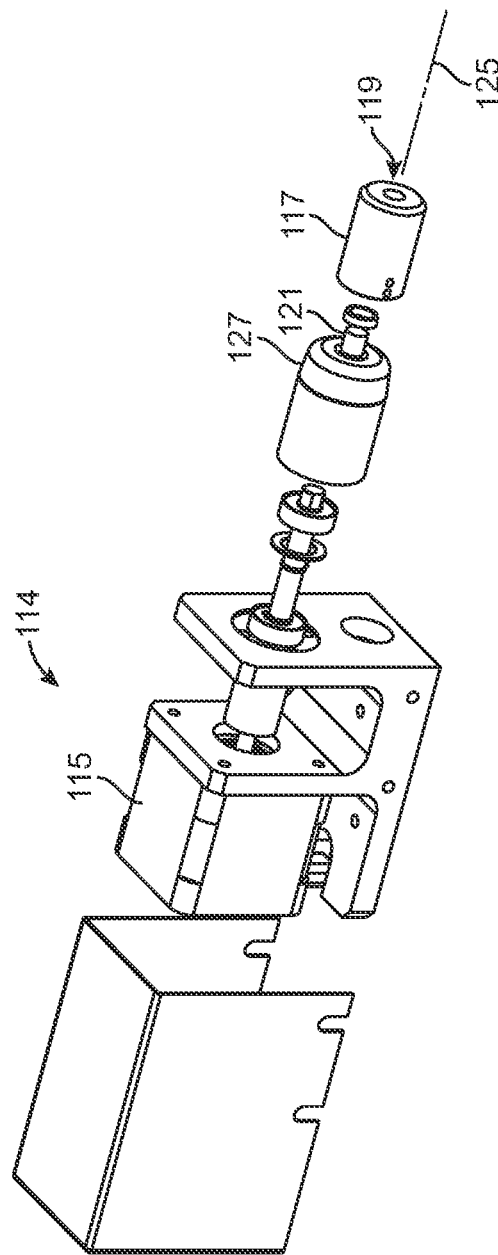

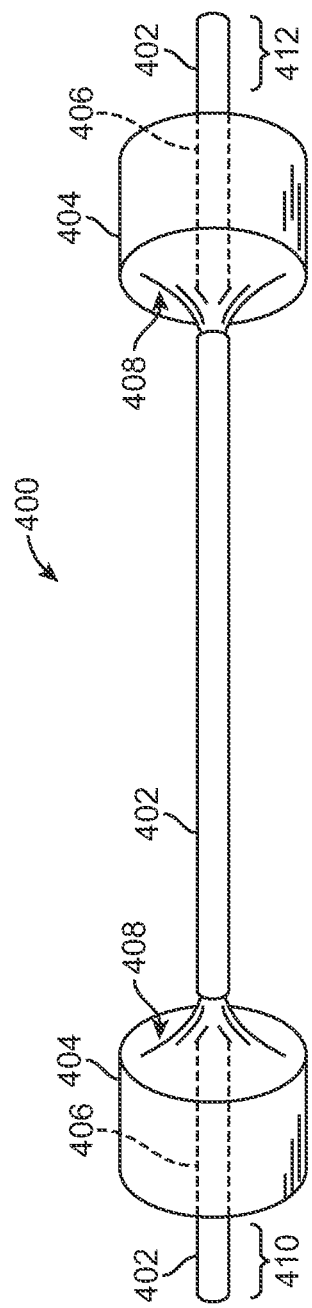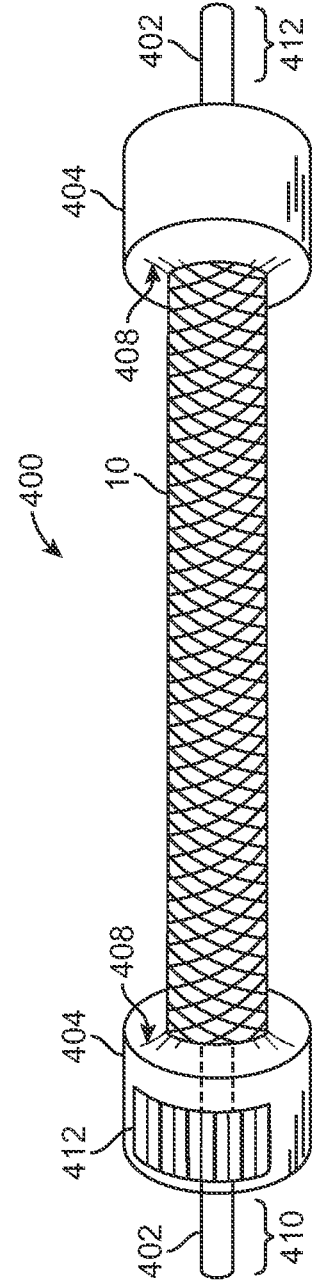
FIG. 8A
FIG. 8B

SYSTEM AND METHOD FOR COATING A MEDICAL DEVICE

FIELD OF THE INVENTION

Briefly and in general terms, the present invention generally relates to coating a medical device, more specifically, to a system and method for coating a stent.

BACKGROUND OF THE INVENTION

In percutaneous transluminal coronary angioplasty (PTCA), a balloon catheter is inserted through a brachial or femoral artery, positioned across a coronary artery occlusion, and inflated to compress against atherosclerotic plaque to open, by remodeling, the lumen of the coronary artery. The balloon is then deflated and withdrawn. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical bypass operation. Stents are used to address these issues. Stents are small, intricate, implantable medical devices and are generally left implanted within the patient to reduce occlusions, inhibit thrombosis and restenosis, and maintain patency within vascular lumens such as, for example, the lumen of a coronary artery.

The treatment of a diseased site or lesion with a stent involves both delivery and deployment of the stent. Stent delivery refers to introducing and transporting the stent through an anatomical lumen to a desired treatment site, such as a lesion in a vessel. An anatomical lumen can be any cavity, duct, or a tubular organ such as a blood vessel, urinary tract, and bile duct. Stent deployment corresponds to expansion of the stent within the anatomical lumen at the region requiring treatment. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen with the stent remaining at the treatment location.

In the case of a balloon expandable stent, the stent is mounted about a balloon disposed on the catheter. Mounting the stent typically involves compressing or crimping the stent onto the balloon prior to insertion in an anatomical lumen. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

Stents are often modified to provide drug delivery capabilities to further address thrombosis and restenosis. Stents may be coated with a polymeric carrier impregnated with a drug or therapeutic substance. A conventional method of coating includes applying a composition including a solvent, a polymer dissolved in the solvent, and a therapeutic substance dispersed in the blend to the stent by immersing the stent in the composition or by spraying the composition onto the stent. The solvent is allowed to evaporate, leaving on the stent strut surfaces a coating of the polymer and the therapeutic substance impregnated in the polymer.

The application of a uniform coating with good adhesion to a substrate can be difficult for small and intricate medical devices, such as certain stents for coronary and peripheral arteries. Such stents can be quite small, typically having an overall diameter of only a few millimeters and a total length of several millimeters. Also, such stents are often in the form of a fine network or mesh of thin struts which provide support or push against the walls of the anatomical lumen in which the stent is implanted.

Figure 14:
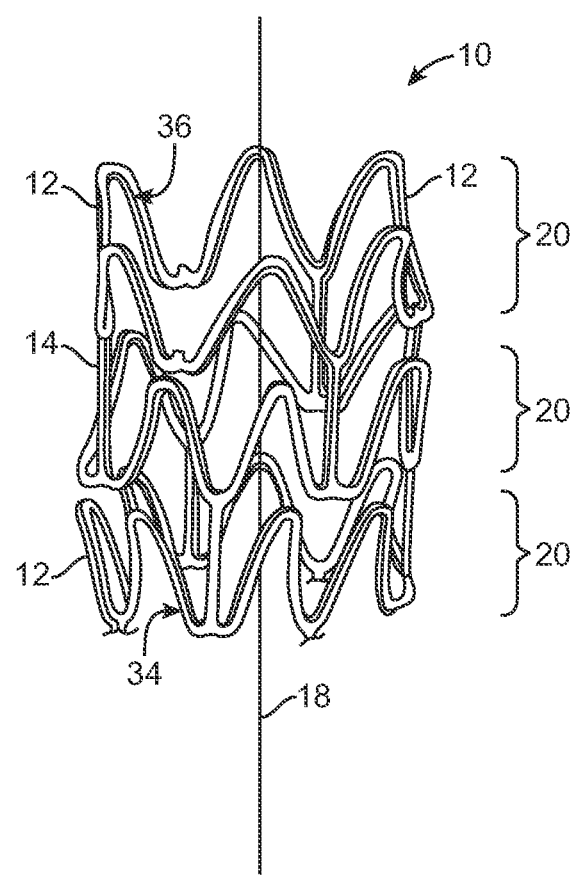

For example, FIG. 14 shows an upper portion of a stent 10 having an overall body shape that is hollow and tubular. The stent can be made from wires, fibers, coiled sheet, with or without gaps, or a scaffolding network of rings. The stent can have any particular geometrical configuration, such as a sinusoidal or serpentine strut configuration, and should not be limited to what is illustrated in FIG. 14. The variation in stent patterns is virtually unlimited. The stent can be balloon expandable or self-expandable, both of which are well known in the art.

Figure 15:
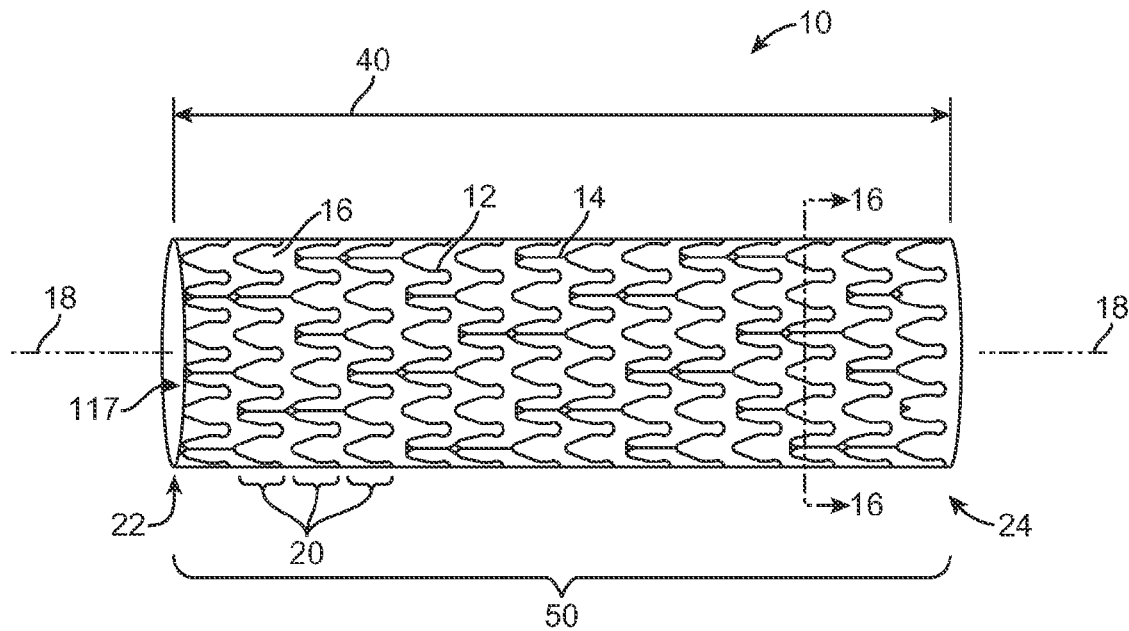

FIGS. 14 and 15 show stents with two different stent patterns. The stents are illustrated in an uncrimped or expanded state. In both FIGS. 14 and 15, the stent 10 includes many interconnecting struts 12, 14 separated from each other by gaps 16. The struts 12, 14 can be made of any suitable material, such as a biocompatible metal or polymer. The polymer could also be a bioabsorbable polymer. The stent 10 has an overall longitudinal length 40 measured from opposite ends, referred to as the distal and proximal ends 22, 24. The stent 10 has an overall body 50 having a tube shape with a central passageway 17 passing through the entire longitudinal length of the stent. The central passageway has two circular openings, there being one circular opening at each of the distal and proximal ends 22, 24 of the overall tubular body 50. A central axis 18 runs through the central passageway in the center of the tubular body 50. At least some of the struts 12 are arranged in series to form sinusoidal or serpentine ring structures 20 that encircle the central axis 18.

Figure 16:
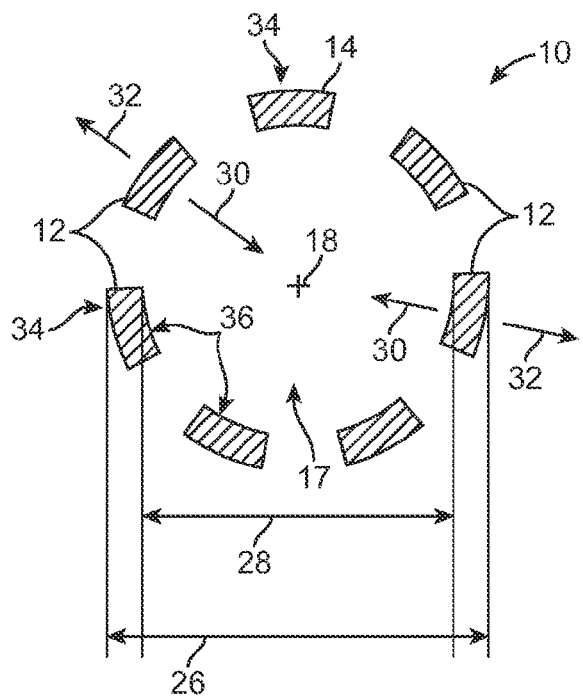

FIG. 16 is an exemplary cross-sectional view of the stent 10 along line 16-16 in FIG. 15. There can be any number of struts 12, 14 along line 16-16, which runs perpendicular to the central axis 18 of the stent 10. In FIG. 16, the cross-section of seven struts 12, 14 are shown for ease of illustration. The struts 12, 14 in cross-section are arranged in a circular pattern having an outer diameter 26 and an inner diameter 28. The circular pattern encircles the central axis 18. A portion of the surface of each strut faces radially inward in a direction 30 facing toward the central axis 18. A portion of the surface of each strut faces radially outward in a direction 32 facing away from the central axis 18. The various strut surfaces that face radially outward collectively form the outer surface 34 of the stent 10. The various strut surfaces that face radially inward collectively form the inner surface 36 of the stent 10.

The terms "axial" and "longitudinal" are used interchangeably and relate to a direction, line or orientation that is parallel or substantially parallel to the central axis of a stent or a central axis of a cylindrical structure. The term "circumferential" relates to a direction along a circumference of a stent or a circular structure. The terms "radial" and "radially" relate to a direction, line or orientation that is perpendicular or substantially perpendicular to the central axis of a stent or a central axis of a cylindrical structure.

Coating of the thin network of struts often leads to pooling or webbing of the coating substance where struts meet, non-uniform coating thickness and distribution, delamination, contamination. Many spray coating systems are inefficient and produce a high incidence of coating defects due in part to insufficient control of the spray and dry environment.

A coating process may require the application of several coating substances applied separately as a primer layer, a drug carrying reservoir layer, and a top coat or drug diffusion barrier. Each coating layer can involve the use of multiple compounds to form a blend of solvent, polymer, and drug. Also, a coating process may includes multiple spray and dry cycles to form a desired thickness for each coating layer. Thus, it can be difficult to keep track of coating cycles and the types or batches of coating substances for each cycle. Keeping track and recording of such details is important for quality and regulatory control. Since the amount of drug on the stent or the desired properties of each coating is directly proportional to the coating thickness and weight, the unique identity of each stent must be tracked as it progresses down the manufacturing line. To ensure accurate tracking, many systems and methods involve a one-piece flow manufacturing model wherein a spray coating machine processes one stent at a time, which can be inefficient and time consuming because of the time require for drying between coats and because of the need for multiple coats on each stent. An approach to increase manufacturing output would be use several spray coating machines in parallel, as in a multi-piece flow manufacturing scheme. A disadvantage of this approach is that it deviates from the one-piece flow manufacturing scheme that controls stent identity in a highly reliable way and, thus, may allow stents to become mixed up from time to time due to loss of tracking identity. Loss of tracking identity causes a stent, or even an entire production lot of stents, to be scrapped to waste.

Another difficulty in producing drug-coated medical devices, such as drug eluting stents, is that the drugs, solvents, and other substances used in the manufacturing process can be dangerous to the health of human operators of manufacturing equipment. In some cases, the drug can be an immunosuppressant, which can have a significant effect even in very small amounts not noticeable by normal smell or sight.

Accordingly, there is a continuing need for a system and a method for coating medical devices that are efficient, reliable, and take into account the health and safety of persons involved in the manufacturing process.

SUMMARY OF THE INVENTION

Briefly and in general terms, the present invention is directed to a system and method for coating a medical device. In some aspects of the present invention, a system and method for coating a medical device involves subjecting alternating groups of medical devices to spraying and drying.

In aspects of the present invention, a system for coating a medical device comprises an enclosure having a first aperture and a second aperture, the first aperture sized to receive a first medical device, the second aperture sized to receive a second medical device. The system further comprises a coating dispenser disposed inside the enclosure, a first device configured to support the first medical device or a first medical device carrier, a second device configured to support the second medical device or a second medical device carrier, a first apparatus disposed outside of the enclosure, the first apparatus configured to move the first device toward and away from the first aperture, and a second apparatus disposed outside of the enclosure, the second apparatus configured to move the second device toward and away from the second aperture independently of movement of the first device toward and away from the first aperture. In detailed aspects, the first device and second device are disposed at opposite sides of the enclosure.

In other aspects of the present invention, a system for coating a medical device comprises a chamber having a first aperture sized to receive the medical device, a coating dispenser inside the chamber, a gas dispenser configured to discharge gas along a gas flow path outside the chamber, a proximal support element configured to support a proximal portion of the medical device or a proximal portion of a medical device carrier, and an apparatus configured to move the proximal support element toward the chamber along a travel path that intersects the gas flow path. In further aspects, the system further comprises a temperature sensor, wherein the apparatus is configured to move the temperature sensor along a sensor travel path that intersects the gas flow path.

In other aspects of the present invention, a system for coating a medical device comprises an isolation wall, the isolation wall separating a spray area and a drying area, the isolation wall including an access aperture sized to receive the medical device. The system further comprises a coating dispenser configured to discharge a coating substance in the spray area, a gas dispenser configured to discharge a gas in the drying area, a support device including a support element configured to retain the medical device or a medical device carrier, and an assembly configured to move the coating dispenser in the spray area and to move the support device in the drying area. In detailed aspects, the assembly is configured to move the coating dispenser in a first travel path and to move the support device in a second travel path parallel or substantially parallel to the first travel path.

In other aspects of the present invention, a system for coating a medical device comprises at least one spray-dry apparatus. Each spray-dry apparatus includes a spray enclosure including at least two access apertures, each access aperture sized to receive a medical device. Each spray-dry apparatus further includes at least two retention devices, there being one retention device associated with each one of the access apertures, each retention device configured to retain a medical device or a medical device carrier. Each spray-dry apparatus further includes a coating dispenser inside the spray enclosure, a gas dispenser outside the spray enclosure, the gas dispenser configured to discharge a gas, and an assembly configured to move the coating dispenser and to move each retention device.

In detailed aspects, the system further comprises an outer enclosure containing the at least one spray-dry apparatus. The system further comprises a first transport apparatus extending into the outer enclosure from outside the outer enclosure, the first transport apparatus configured to carry and move the medical device or the medical device carrier from outside the outer enclosure to inside the outer enclosure. The system further comprises a second transport apparatus extending out of the outer enclosure from inside the outer enclosure, the second transport apparatus configured to carry and move the medical device or the medical device carrier from inside the outer enclosure to outside the outer enclosure. The system further comprises a third transport apparatus inside the outer enclosure, the third transport apparatus including a gripper and a mechanism, the gripper configured to engage the medical device or the medical device carrier, the mechanism configured to move the gripper from a first position to a second position and from the second position to a third position, the first position adjacent the first transport apparatus, the second position adjacent to any one of the retention devices, the third position adjacent to the second transport device.

In some aspects of the present invention, a method for coating a medical device comprises moving a first medical device into a spray area, applying a coating on the first medical device in the spray area, moving the first medical device out of the spray area to a drying area after the first medical device is coated, moving a second medical device into the spray area during or after moving the first medical device to the drying area, discharging a gas onto the first medical device in the drying area; and applying a coating on the second medical device in the spray area while discharging the gas onto the first medical device in the drying area. In detailed aspects, the method moving the first medical device out of the spray area to the drying area includes moving the first medical device through an aperture formed in a wall separating the spray area from the drying area.

The features and advantages of the invention will be more readily understood from the following detailed description which should be read in conjunction with the accompanying drawings.

BRIEF DESCRIPTION OF THE DRAWINGS

FIG. 1 is a perspective view of a system for coating medical devices, showing a transparent enclosure, conveyor assemblies passing through the enclosure, isolator spray enclosures within the transparent enclosure, spindle assemblies for spinning stents and moving the stents in and out of the isolator enclosures, and a coating solution enclosure.

FIG. 2 is a partial detailed view of the system of FIG. 1, showing the isolator spray enclosures and the spindle assemblies.

FIGS. 3A and 3B are perspective views of a spray-dry assembly from the front and the rear, respectively, showing the isolator spray enclosures and the spindle assemblies of FIG. 2 and devices for moving the spindle assemblies in and out of the isolator enclosures.

FIGS. 4A and 4B are perspective view of the spindle assembly of FIG. 2, showing the spindle assembly in an assembled and an exploded, disassembled state, respectively.

FIGS. 5A-5D are perspective views of an spray enclosure subassembly including the enclosure of FIG. 2, showing a left-front view, a left-rear view, a right-front view, and a partially exploded view, respectively.

FIG. 6 is a perspective view of a spray nozzle subassembly, showing spray coating nozzles and devices for linearly translating the spray coating nozzles in the spray isolator enclosures of FIG. 2.

FIGS. 7A and 7B are perspective views of a dryer nozzle subassembly, showing a nozzle for discharging gas outside of the spray isolator enclosures of FIG. 2.

FIGS. 8A and 8B are perspective views of a medical device carrier and a stent carried on the carrier, respectively.

FIG. 9 is a perspective view of one of the conveyor assemblies of FIG. 1, showing a holder for the medical device carrier of FIGS. 8A and 8B.

FIG. 10 is a perspective view of the coating solution enclosure of FIG. 1, showing containers of coating solution, pumps, and fluid conduits connecting the containers and the pumps.

FIG. 11 is a block diagram of the system of FIG. 1

FIG. 12 is a schematic plan view of the spray-dry assembly of FIG. 3A.

FIGS. 13A-13D are schematic diagrams of a method for coating and drying groups of medical devices.

FIG. 14 is a perspective view of a portion of a stent.

FIGS. 15 and 16 are perspective and cross-sectional views, respectively, of a stent.

DETAILED DESCRIPTION OF THE PREFERRED EMBODIMENTS

Referring now in more detail to the exemplary drawings for purposes of illustrating embodiments of the invention, wherein like reference numerals designate corresponding or like elements among the several views, there is shown in FIG. 1 a stent coating system 100 providing a controlled manufacturing environment for transporting, spraying, and drying of a medical device.

In use, a person stands at position 102 outside of a transparent shielded enclosure 104 and places stents to be coated on an inbound conveyor assembly 106. Another person stands at position 108 outside of the shielded enclosure 104 and removes coated stents from an outbound conveyor assembly 110. The stents are not handled directly. Each stent is individually carried on separate carrying devices, referred to herein as a "mandrel," and may be moved independently of each other from point to point during the coating process via direct manipulation of the mandrel. The mandrel is configured to retain the stent in vertical and horizontal orientations. The mandrel can take a variety of forms, and may contact the inner surface, outer surface, or both inner and outer surface of the stent.

The inbound conveyor assembly 106 moves the mandrels with stents through a small opening in the shielded enclosure 104, from a position outside the shielded enclosure to a position inside the shielded enclosure. When inside, the mandrels with stents are automatically moved by a gripper 112 of a robotic mechanism from the inbound conveyor assembly 106 to spindle subassemblies 114. The robotic mechanism includes vertical and horizontal rails, and may further include helical drives, gears, belts, and/or motors to allow the gripper 112 to translate vertically in the Y-axis direction (up and down) and horizontally in the X-axis direction (left and right). The gripper 112 may include a pair of articulating members configured to move relative to each other to allow the articulating members to pinch or squeeze onto a portion of the mandrel and to release the mandrel.

In the various figures, the illustrated X-, Y- and Z-axes are orthogonal. Directions in the X-axis are horizontal or substantially horizontal. Directions in the Y-axis are vertical and are perpendicular to the X-axis. Directions in the Z-axis are horizontal or substantially horizontal. Directions in the Z-axis are perpendicular to the X-Y plane formed by the X- and Y-axes.

FIGS. 3A and 3B show various views of a spray-dry assembly 200, the parts of which will be explained below in further detail. Each spray-dry assembly includes a spray isolator enclosure 116 configured to prevent escape of spray coating substances to areas outside the spray isolator enclosure. In the illustrated embodiment of FIGS. 1 and 2, the system 100 includes two spray-dry assemblies 200. It will be appreciated that any number of spray-dry assemblies 200 may be implemented together.

With reference to FIGS. 1, 2B, 3A, and 3B, each spay-dry assembly 200 includes four spindle subassemblies 114. The spray isolator enclosure 116 has a left-side pair of spindle subassemblies 114*a* to the left of the enclosure, and a right-side pair of spindle subassemblies 114*b* to the right of the enclosure. After the left-side spindle 114*a* assemblies are loaded with stents, the spindle subassemblies slide the stents inside the spray isolator enclosure where they are coated by a coating dispenser having a pair of spray nozzles 122. The stents pass through access apertures 113 formed through sidewalls of the enclosure 116. While the stents are spray coated inside the enclosure 116, the spindle subassemblies 114 axially rotate the stents about the individual stent central axes.

FIGS. 4A and 4B shows details for each spindle subassembly 114, which includes bearings, couplings, and an electric motor 115 that rotates a holding element 117 configured to retain a mandrel. The holding element 117 includes an aperture 119 that receives a portion of a mandrel. A magnet 121 inside the aperture 119 ensure that the mandrel does not inadvertently slip away from holding element 117 and to ensure that the mandrel rotates with the holding element. The holding element 117 and the magnet 121 function as a retention device that retains the mandrel. When the motor 115 is activated, the holding element 117 rotates in a circumferential direction 123 about an axis of rotation 125. In some embodiments, the central axis of the stent is coaxial with the axis of rotation 125.

Figure 6:
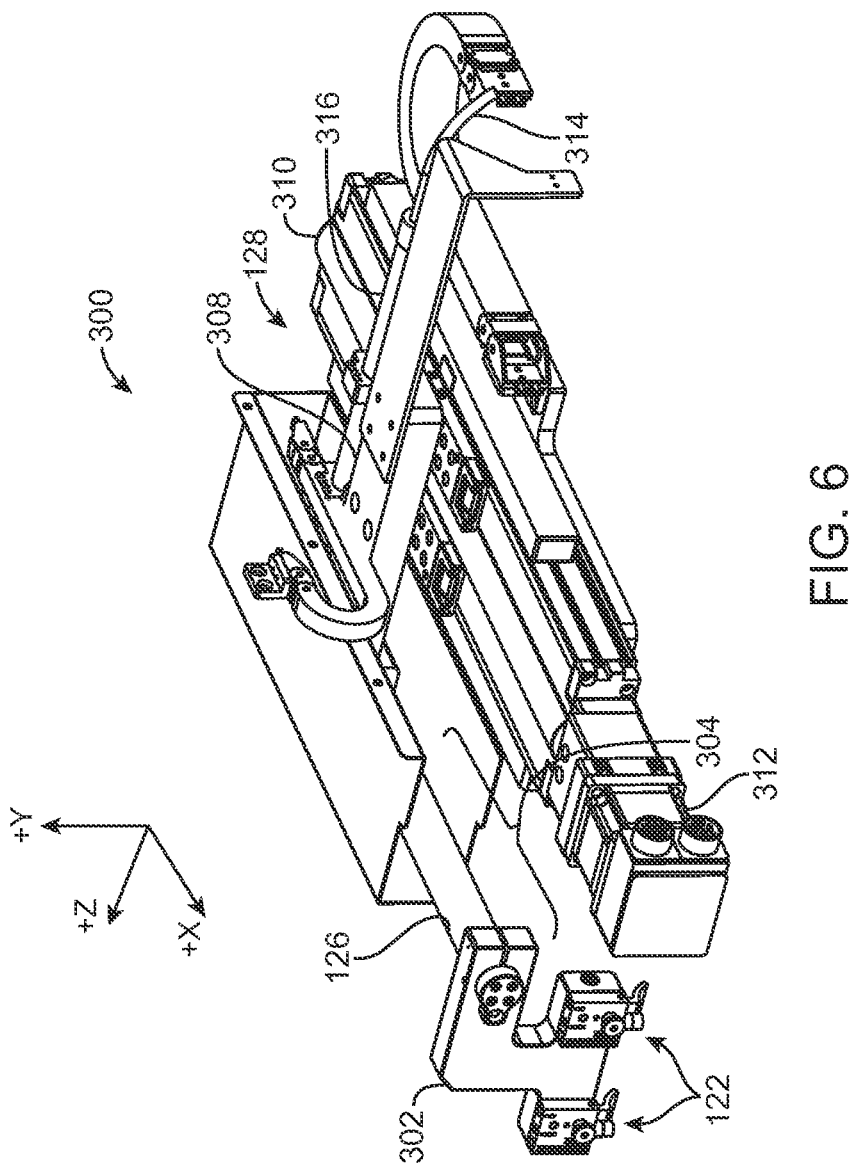
Figure 7A:
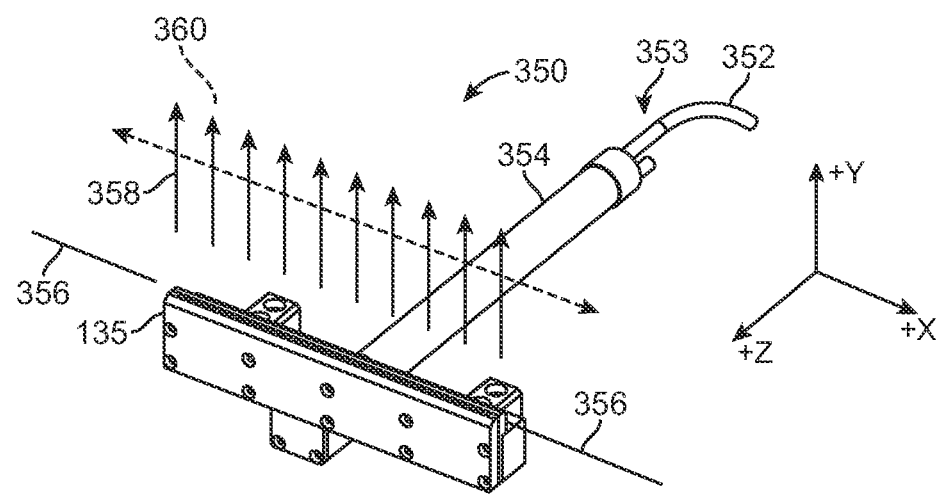

FIGS. 5A-D show various views of a spray enclosure subassembly 250 that forms a part of each spray-dry assembly 200. FIG. 6 shows a spray nozzle subassembly 300 that forms a part of each spray-dry assembly 200. FIG. 7A shows a dryer nozzle subassembly 350, there being four dryer nozzle subassemblies for each spray-dry assembly 200.

Figure 5A:
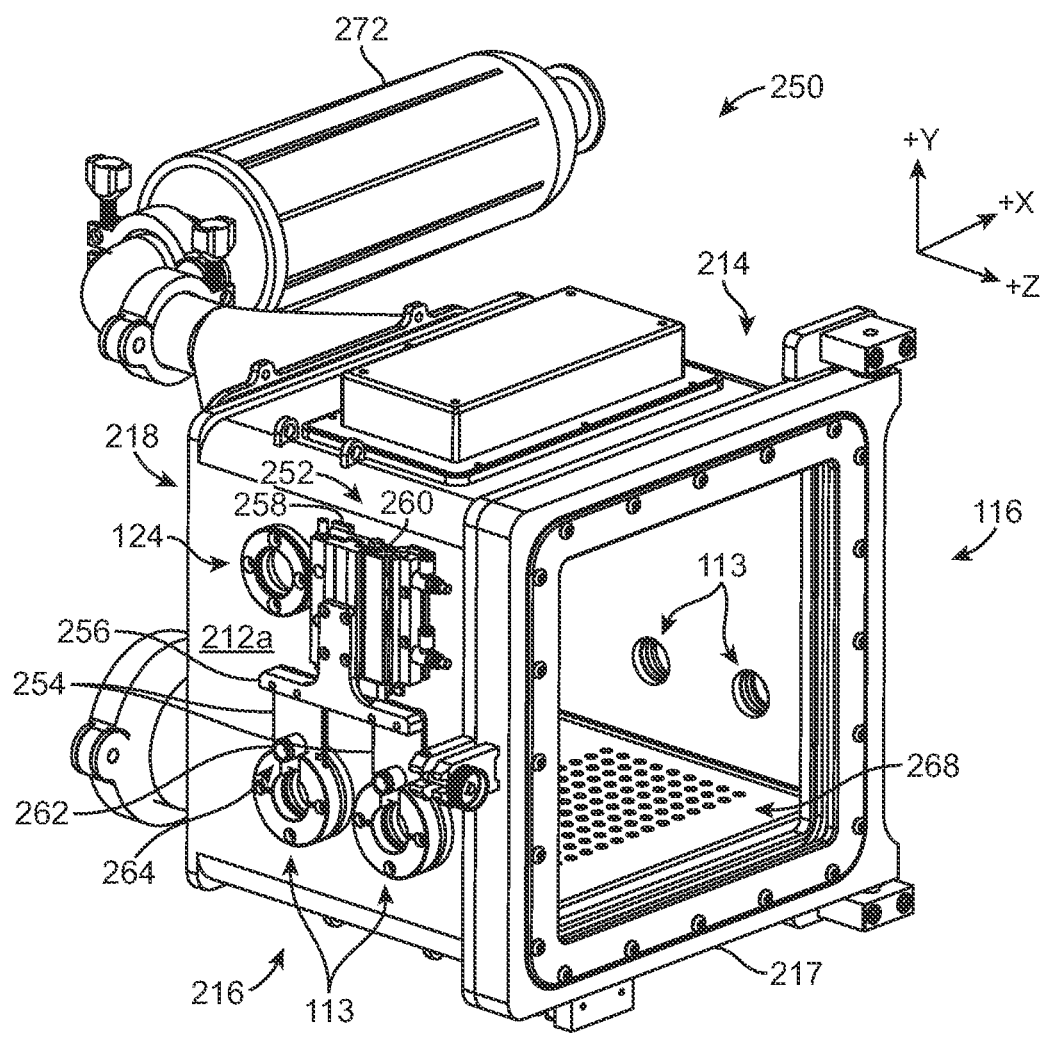
Figure 5B:
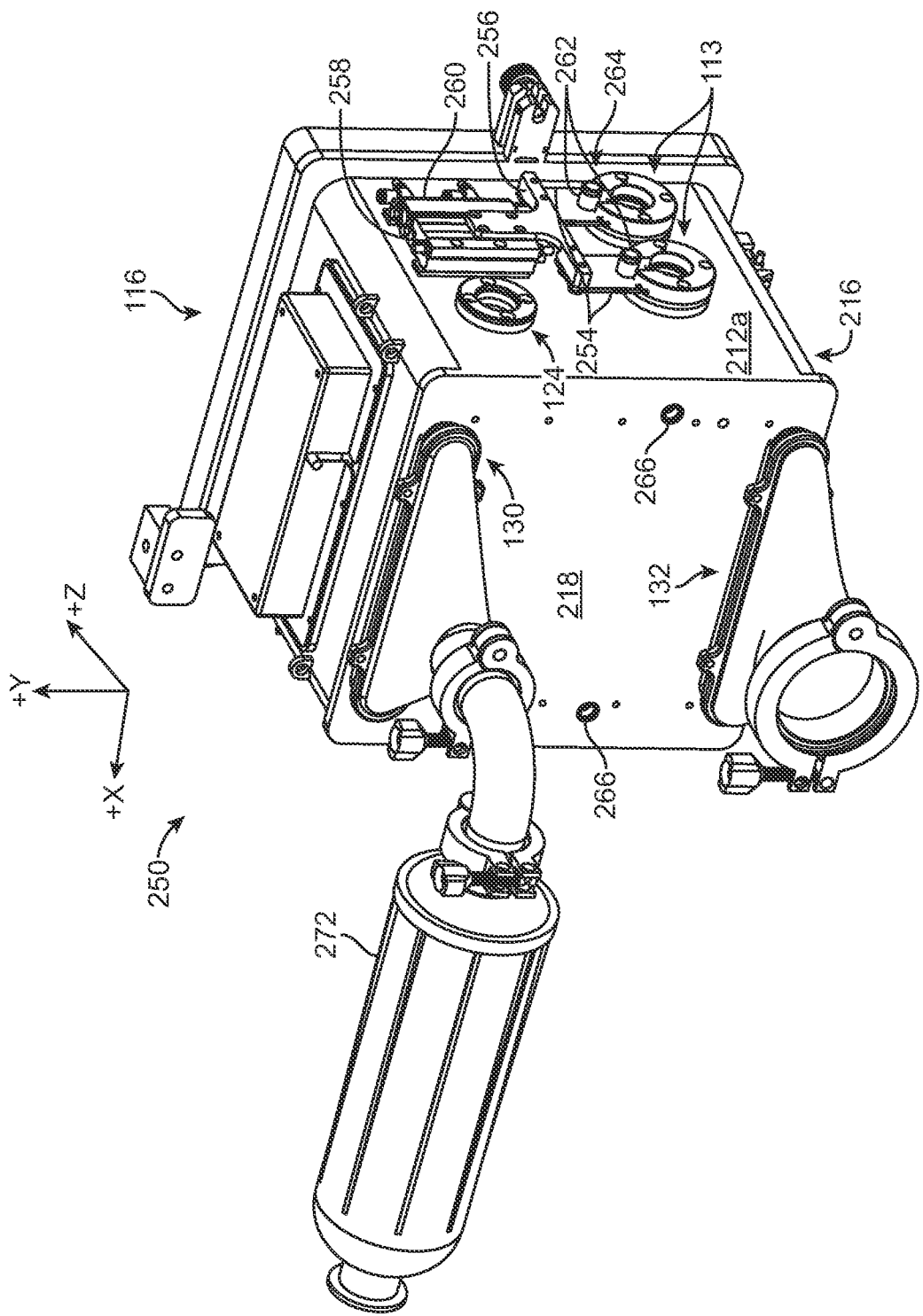
Figure 5C:
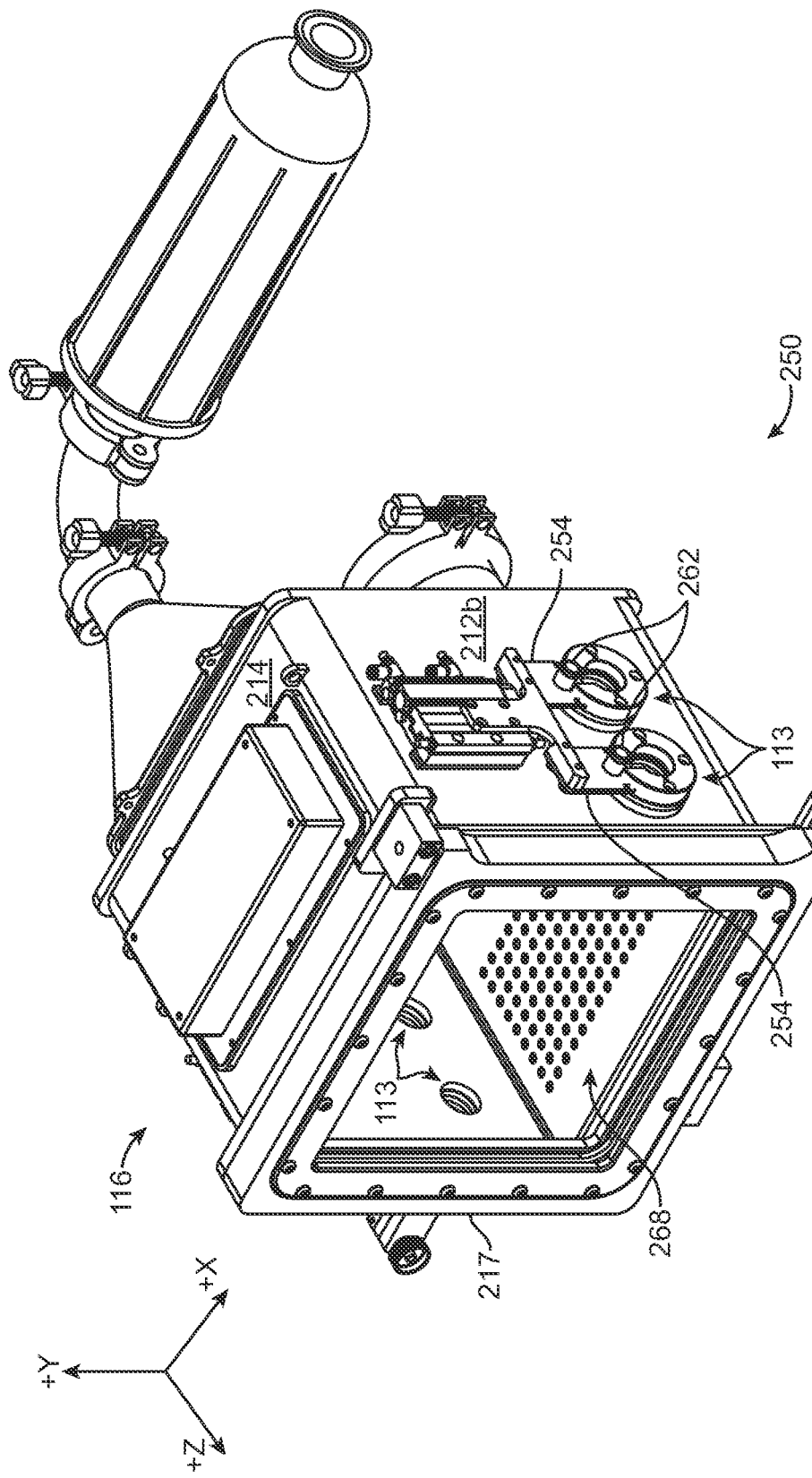
Figure 5D:
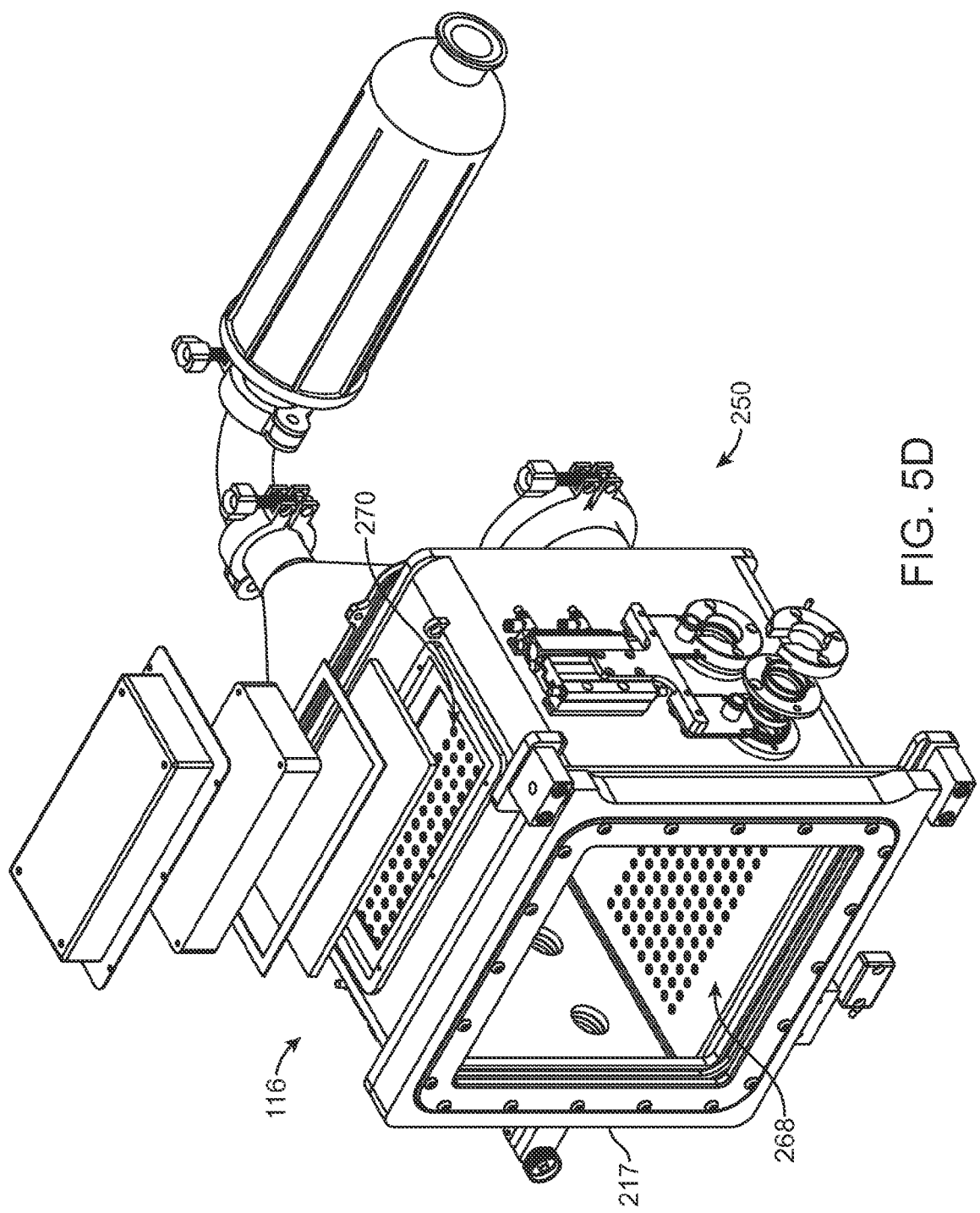

As shown in FIGS. 5A and 5B, an upper portion of each spray isolator enclosure 116 has a side opening 124 through which a shaft 126 (FIG. 6) slides in and out. As shown in FIG. 6, one end of the shaft 126 carries a pair of spray nozzles 122 that discharge a coating substance on a pair of stents that may be inside the spray isolator enclosure 116. The other end of the shaft 126 is attached to a mechanism 128 located outside of the spray isolator enclosure. The mechanism 128 linearly translates the shaft 126, thereby moving the pair of spray nozzles 122 across the entire overall length of the stents inside the spray isolator enclosure 116.

The spray isolator enclosure 116 is connected to a vacuum system that draws filtered air into an inlet 130 (FIG. 6) located at the upper portion of the spray isolator enclosure. An outlet 132 (FIG. 5B) at a bottom portion 126 of the enclosure draws the air and fumes from the coating substance out of the spray isolator enclosure 116.

While stents are being sprayed inside the spray isolator enclosure 116, a temperature transducer 134 (FIG. 3A) at each of the left-side spindle subassemblies 114a measures the air drying temperature coming out of a pair of dryer nozzles 135 located to the left of the spray isolator enclosure 116 and below the left-side spindle subassemblies 114a. The air drying temperature is adjusted as needed based on readings from the temperature transducers 134. After the stents have been sprayed, the left-side spindle subassemblies 114a slide the stents out of the spray isolator enclosure 116 to a position above the left-side dryer nozzles 135a which dry the stents. The spindle subassemblies 114a axially rotate the stents while the stents are being dried.

While the stents are being dried, the right-side spindle subassemblies 114b slide another pair of stents (right-side stents) into the spray isolator enclosure 116. While the right-side stents are sprayed inside the spray isolator enclosure 116, the left-side stents are being dried outside. Also, a transducer 134, one on each right-side spindle subassembly 114b measures the air drying temperature coming out of a pair of dryer nozzles 135 to the right of the spray isolator enclosure 116 and below the right-side spindle subassemblies 114b. The air drying temperature is adjusted as needed based on readings from the transducers 134. After the right-side stents have been sprayed, the right-side spindle subassemblies 114b slide the right-side stents out of the spray isolator enclosure 116 to a position above the right-side dryer nozzles 135b which dry the stents.

While the right-side stents are being dried, the left-side stents are returned into the spray isolator enclosure 116. The process of spraying and drying is repeated any number of times, as may be needed to form a coating with a desired thickness or desired amount of drug.

When a stent has the desired coating, the mandrel carrying the stent is removed from the spindle subassembly 114 by the gripper 112 and placed on the outbound conveyor assembly 110, where it is moved out of the shielded enclosure 104.

The above described process is performed for each of the spray isolator enclosures 116 inside the shielded enclosure 104, thereby allowing up to eight stents to be processed in a staggered manner inside the shielded enclosure at any one time.

FIGS. 8A and 8B show a mandrel 400 for carrying a stent 10. The mandrel includes a rod 402 and two end pieces 404 on the rod 402. The end pieces 404 have through holes 406 sized to receive the rod. Each end piece 404 has a tapered, conical surface 408 configured to engage the ends of the stent 10. The conical surfaces 408 face toward the middle of the rod 402 and face each other. At least one of the end pieces 404 is configured to slide off the rod 402 to allow the stent 10 to be mounted over and around the rod. The rod 402 passes through the central passage of the stent without contacting the inner surface of the stent. There is a protruding portion 410 at the proximal end of the rod 402. The protruding portion 410 is configured to fit inside the aperture 119 (FIG. 4A) of the spindle subassembly 114. The rod includes a magnetic material that is attracted to the magnet 121 of the spindle subassembly 114.

In the illustrated embodiment, the spindle subassembly is configured to support and retain a mandrel or other medical device carrier. In other embodiments, the spindle subassembly is configured to support and retain the medical device directly. For example, the spindle subassembly can include an elongate member sized to fit through the central passageway of a stent and thereby support the stent by its inner surface.

Figure 9:
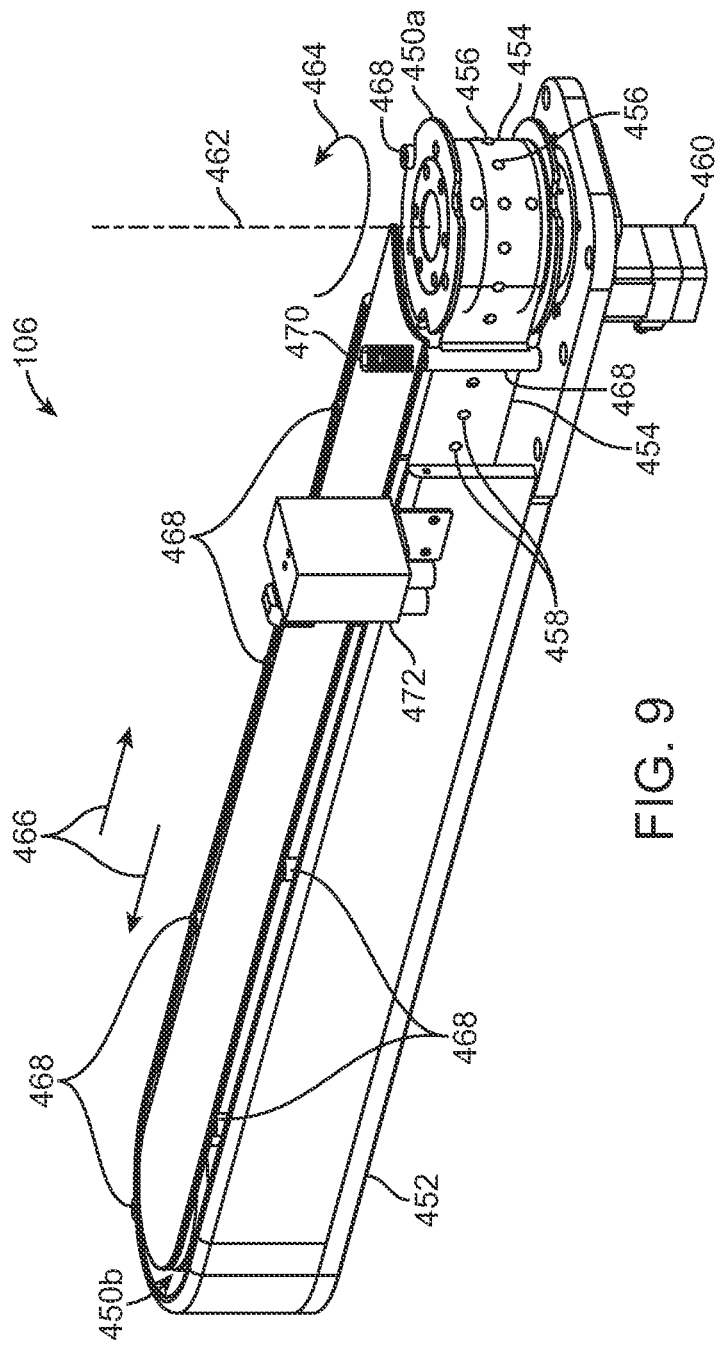

FIG. 9 shows the inbound conveyor assembly 106. Two rollers 450 are mounted on opposite end portions of a base plate 452. A continuous belt 454 is kept in tension by the rollers. One of the rollers, referred to as the driver roller 450a, is connected to an electric motor 460 beneath the base plate 452. The electric motor 460 rotates the driver roller 450a about the roller central axis 462. Protruding teeth elements 456 on the rollers 450 extend though holes 458 formed in the belt 454 to ensure that rotation 464 of the rollers 450 causes movement 466 of the belt 454. Cylindrical mandrel holders 468 are attached on the belt 454 and are spaced equally apart from each other on belt. Each mandrel holder 468 includes a top surface into which a hole is formed. The hole is sized to receive the protruding portion 410 (FIGS. 8A and 8B) of the mandrel 400.

The inbound conveyor assembly 106 includes a proximity sensor 470. The sensor 470 includes a photoelectric transducer that is configured to detect the presence of a mandrel. The sensor 470 is held at a fixed position relative to the robotic mechanism for the gripper 112 (FIG. 1). The sensor 470 allows a microprocessor-based controller to verify that the mandrel has been picked up by the gripper 112 and that the mandrel holder 468 is empty as it travels away from the gripper area.

A barcode reader 472 is attached to a guide member surrounding 474 partially surrounding the belt 454. The barcode reader 472 includes an infrared emitter and infrared sensor configured to read a barcode 412 (FIG. 8B) on the mandrel 400. The barcode 412 may be adapted to uniquely identify the particular stent 10 on the mandrel. The barcode reader 472 allows a microprocessor-based controller in communication with the barcode reader to keep track of the stents that enter the system 100 and to track and record the particular coating substances applied to the stent, the number of coating layers the stent has received, and other processing parameters.

In some embodiments, the outbound conveyor assembly 110 is identical in structure to the inbound conveyor assembly 106 shown in FIG. 9. In other embodiments, the outbound conveyor assembly 110 is assembled as a mirror image of the inbound conveyor assembly 106.

Referring again to FIG. 1, the system 100 includes display monitors 140 for displaying information about the coating process. Information may include without limitation identification of the stents inside the shielded enclosure 104, coating progress for a particular stent inside the shielded enclosure 104, the position of a particular stent on a particular spindle subassembly, whether a particular stent is being dried or being spray coated, and identification of spray coating substances with regard to type and batch.

Figure 2:
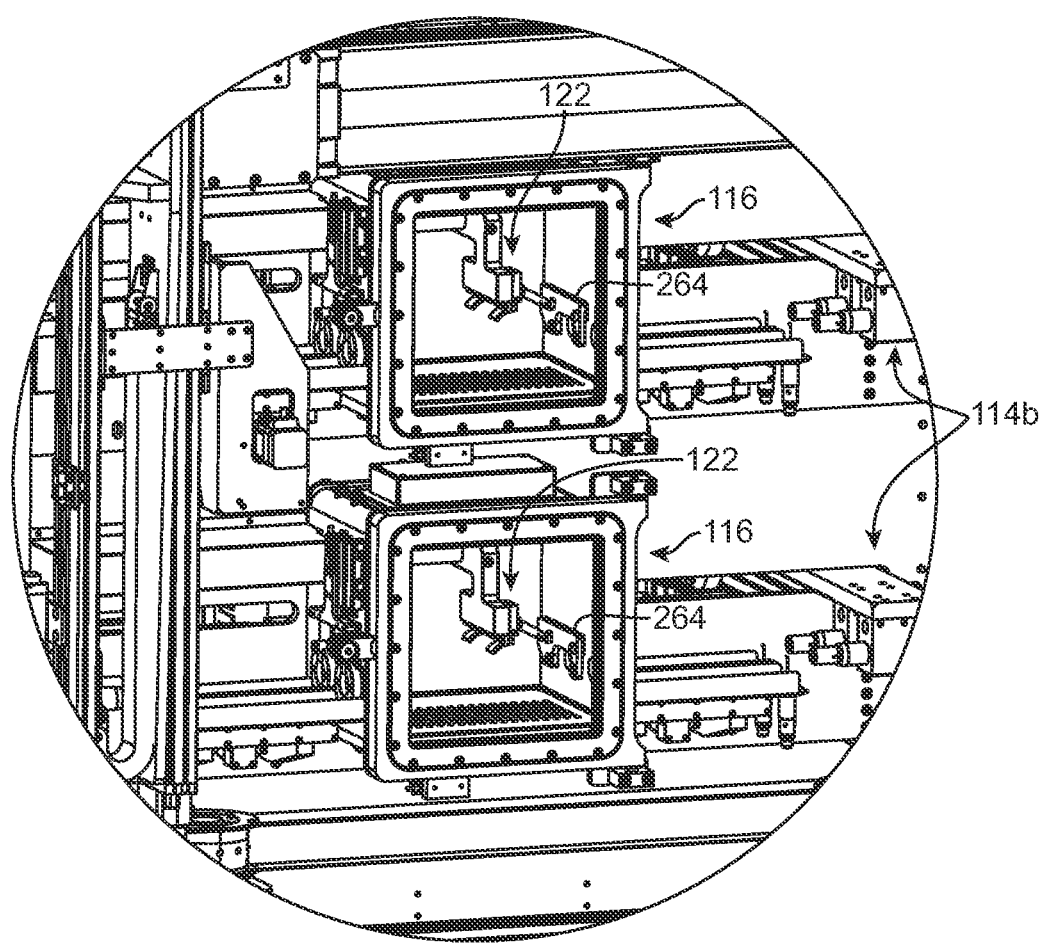
Figure 10:
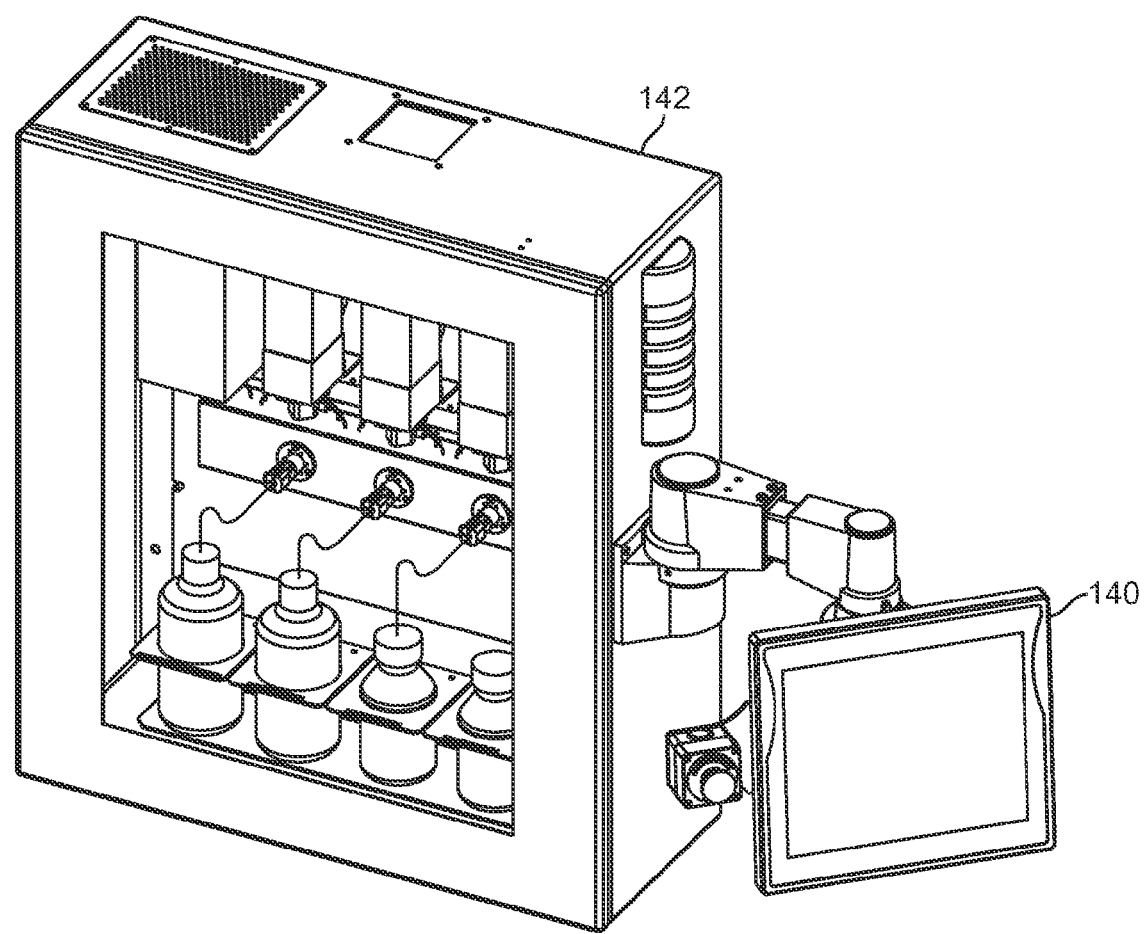

As shown in FIGS. 1 and 10, the system 100 also includes a coating solution enclosure 142 with a transparent door that can be opened to access various bottles and containers which may hold solvents, polymers, drugs, and other substances used for coating. Tubes and pumps connected to the bottles and containers convey the coating substances to the spray nozzles 122 (FIG. 2B) inside each of the spray isolator enclosures 116.

Figure 11:
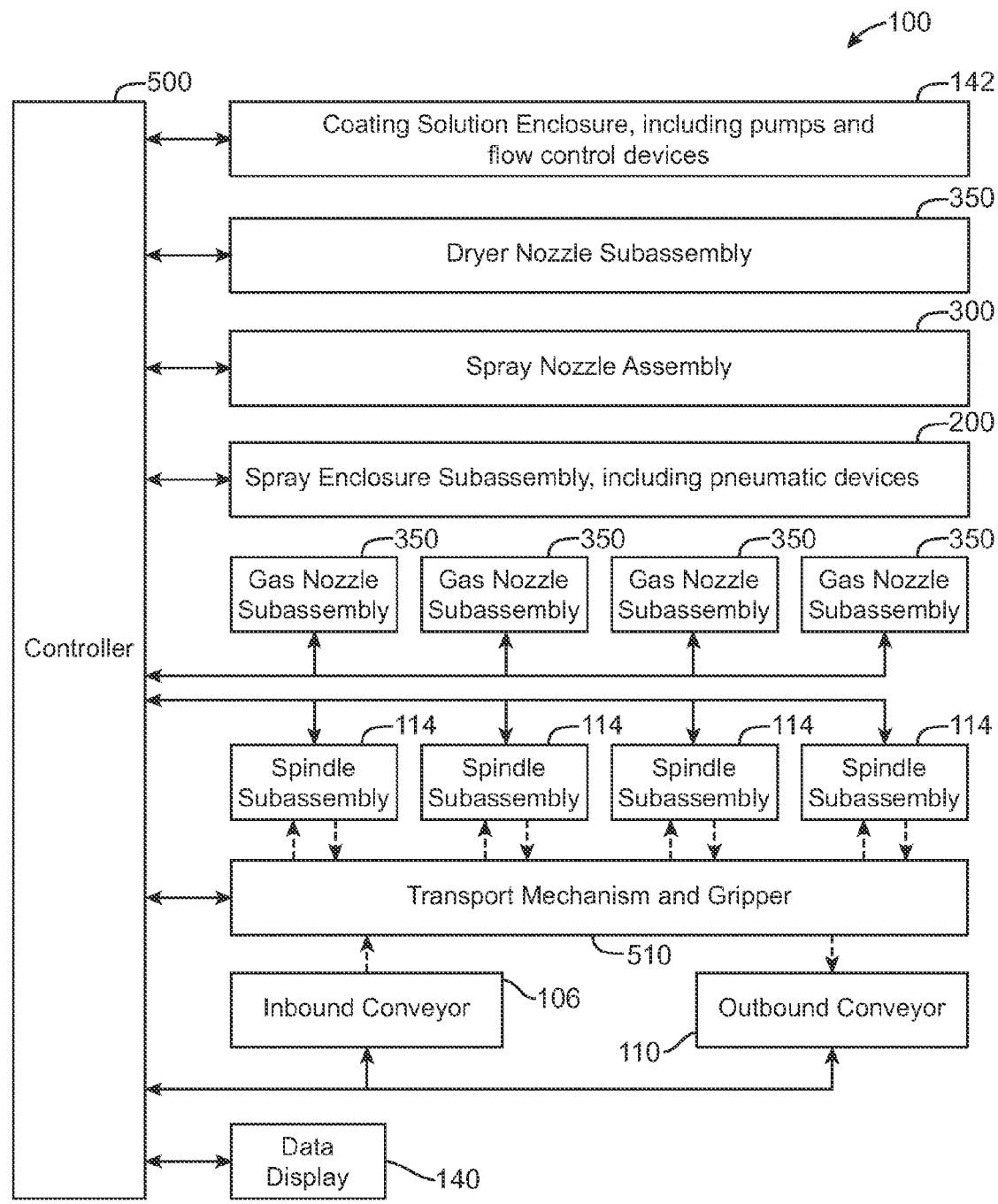

Referring next to FIG. 11, a controller 500 communicates with various parts of the system 100. The controller 500 can be a computer and/or may include several microprocessors and programmable controllers and microcontrollers containing logic for operating the various parts of the system 100 in a coordinated manner. The controller may be located locally within and as an integral part of the system 100. In some embodiments, the controller is located apart from the system 100 and may be configured to control and operate several systems 100.

The controller 500 is configured to control and operate the inbound and outbound conveyor assemblies 106, 110. The controller is configured to send and receive signals from the proximity sensor 470 and the barcode reader 472 of the inbound and output conveyer assemblies 106, 110. The controller is configured to activate and provide power to the conveyor motor 460 of the inbound and output conveyer assemblies 106, 110 to move stents in and out of the system 100. The dashed arrows in FIG. 11 indicate movement of stents to and from parts of the system 100.

The controller 500 is configured to control and operate a transport mechanism 510 of the gripper 112 to move stents from the inbound conveyor assembly 106 to the spindle subassemblies 114, and from the spindle subassemblies to the outbound conveyor assembly 110. The controller 500 is configured to activate and provide power to the mechanism motors to move the gripper along the X- and Y-axes.

The controller 500 is configured to control and operate the spindle subassemblies 114. The controller is configured to activate and provide power to the spindle motors 115 to rotate the mandrels and stents mounted on the mandrels. The controller 500 is configured to activate and provide power to various motors of the spray-dry assemblies 200 (FIGS. 3A and 3B) to linearly translate the spindle subassemblies 114. In some embodiments, the controller 500 is configured to cause movement of the left-side pair of spindle subassemblies 114a into the spray isolator enclosure 116 only during or after the right-side pair of spindle subassemblies 114b move out of the enclosure.

Figure 3A:
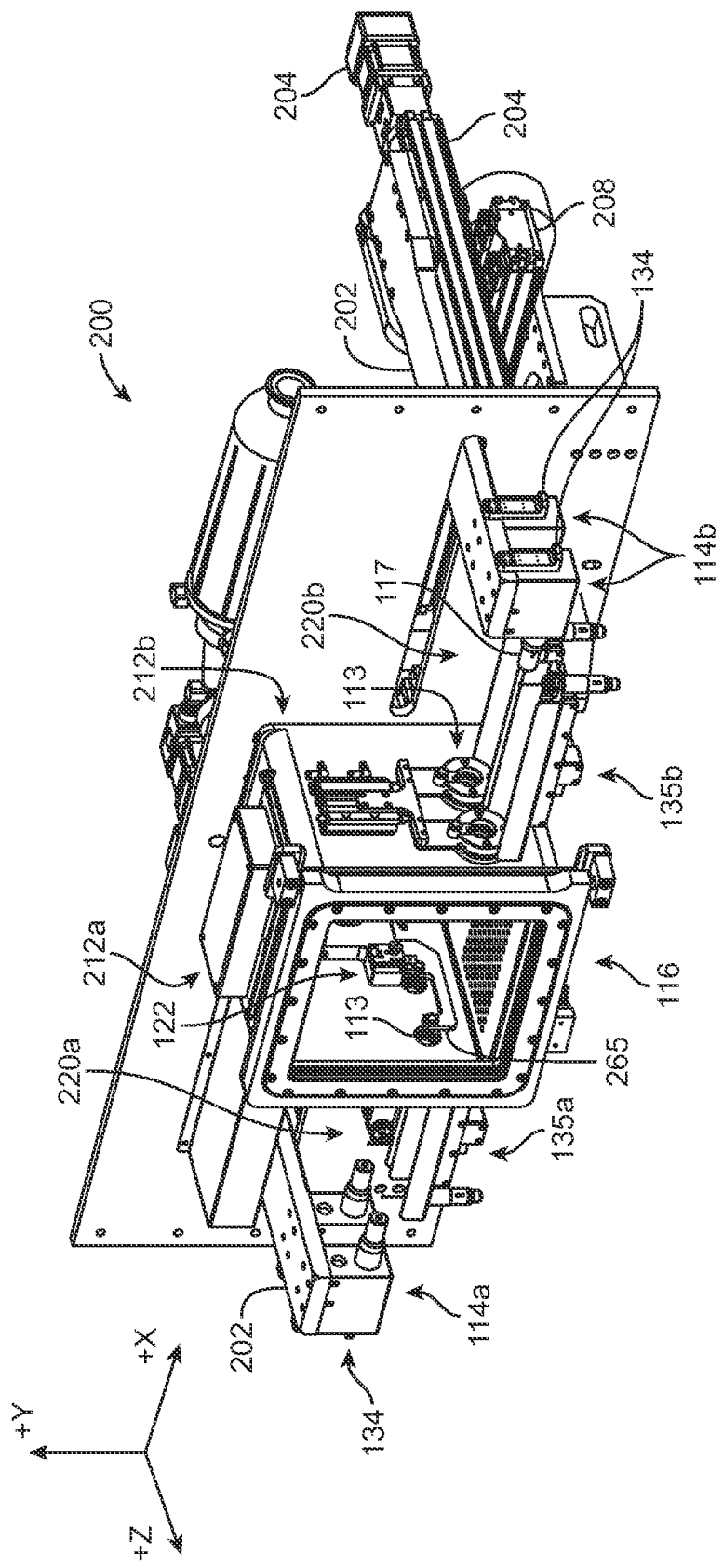
Figure 3B:
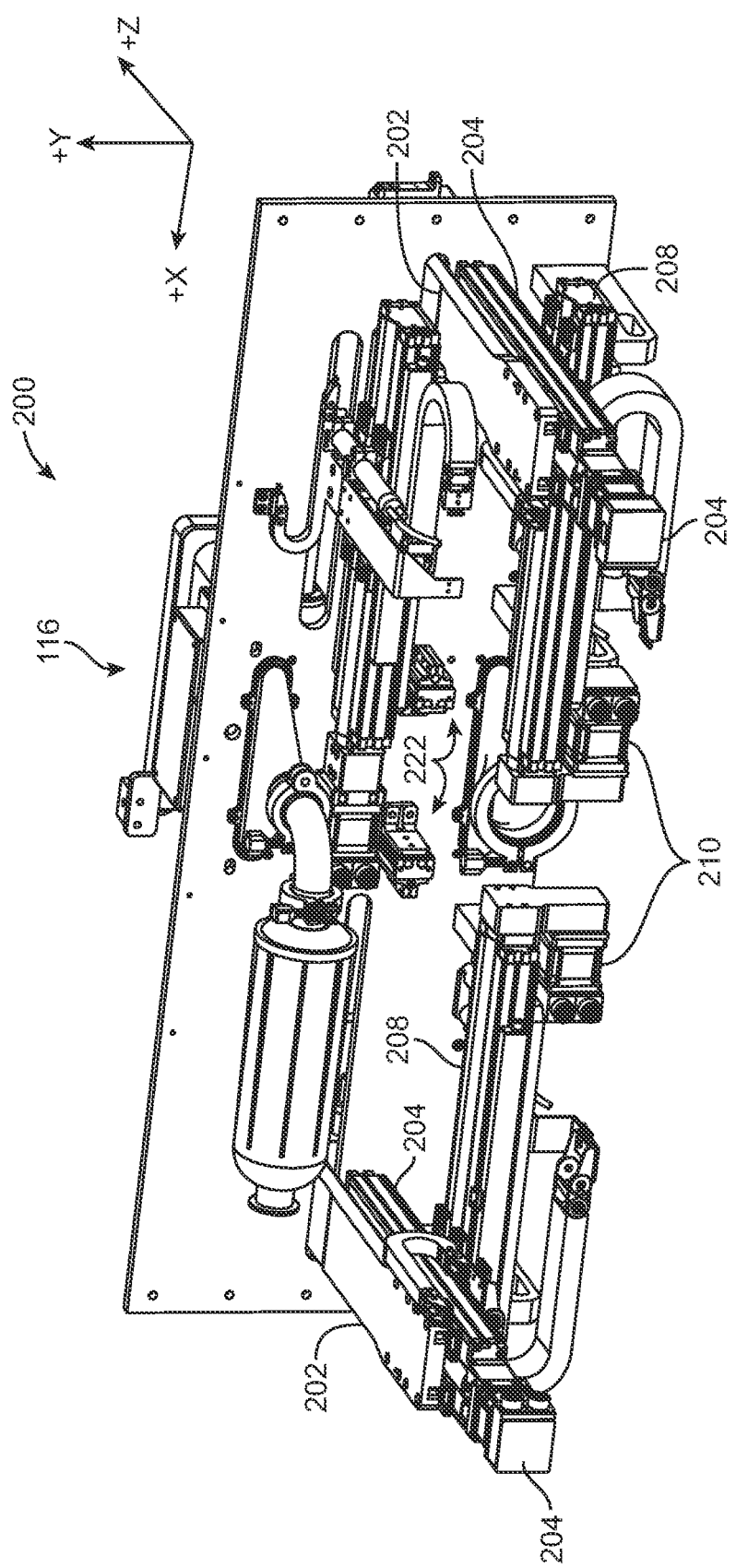

As shown in FIGS. 3A and 3B, each pair of spindle subassemblies 114 (each of the left-side pair 114a and right side pair 114b) is mounted on a support arm 202 mounted on a Z-axis rail 204, which may contain helical drives, gears, belts, and/or other motion transfer elements. A first electric motor 204 on the Z-axis rail 204 is configured to linearly translate in the Z-axis directions the pair of spindle subassemblies 114 on the support arm 202. In this way, pairs of spindle subassemblies 114 may be pushed from a rearward position to a forward position to facilitate loading and unloading of mandrels and stents. FIG. 3A shows all the spindle subassemblies 114 in the rearward position. The rearward position is to the rear of the plane formed by the closed transparent door 206 at the front of the spray isolator enclosure 116. The forward position is in front of the plane formed by the closed transparent door 206.

The Z-axis rail 204 is mounted on an X-axis rail 208, which may contain helical drives, gears, belts, and/or other motion transfer elements. A second electric motor 210 (FIG. 3B) on the X-axis rail 208 is configured to linearly translate in the X-axis the pair of spindle subassemblies 204 on the support arm 202. In this way, pairs of spindle subassemblies 114 may be pushed back and forth relative to the spray isolator enclosure 116, from a distant position to a near position, and back to the distant position. A stent on a spindle subassembly 114, whether supported directly or carried on a mandrel, is located inside the spray isolator enclosure 116 when the spindle subassembly is at the near position and is located outside the spray isolator enclosure when the spindle subassembly is in the distant position. In FIG. 3A, all the spindle subassemblies 114 (left-side and right-side spindle subassemblies 114a, 114b) are shown at the distant position. It is to be understood that in many instances during operation, one pair of spindle subassemblies are in the near position while the other pair of spindle subassemblies in the distant position.

When at the distant position, a pair of spindle subassemblies 114 is located at a predetermined distance away from its adjacent enclosure sidewall. The separation distance is sufficient to allow mandrel and a stent to fit between the spindle subassemblies 114 and the adjacent enclosure sidewall. The separation distance partially defines a drying area 220.

The enclosure 116 has a left-side wall 212a, a right-side wall 212b parallel to the left-side wall, a top wall 214, a bottom wall 216, a hinged transparent front door 217, and a rear wall 218. The left-side and right-side walls 212a, 212b physically isolate the spray area inside the enclosure 116 from the drying area 220. There is a left-side drying area 220a and a right-side drying area 220b.

When at the near position, a pair of spindle subassemblies 114 is located in the drying area and immediately adjacent to a sidewall. In some embodiments, the holding element 117 and base element 127 (FIG. 4A) of the spindle subassembly 114 pass through an access aperture 113 in the sidewall. Thus, when at the near position, the spindle subassembly 114 covers the aperture 113 and prevents spray coating material from flowing out of the spray isolator enclosure 116. In some embodiments, the holding element 117 or a tapered base element 127 (FIG. 4A) at the base of the holding element 117 has a size and shape that tightly seals the access apertures 113 when the spindle subassembly 114 is at the near position. The tight seal prevents escape of solvent fumes and drugs into the surrounding manufacturing environment.

As previously indicated, the coating material that is sprayed onto the stent may include substances that, even in trace amounts, can have an adverse effect on persons involved in manufacturing medical devices. A function of the isolator enclosure 116 is to prevent escape of solvent fumes, drugs, and other chemicals into the surrounding manufacturing environment. The system 100 includes multiple containment features. The isolator enclosure 116 is maintained at a negative pressure relative to the ambient pressure surrounding the system 100. Thus, when shutter doors 254 are opened to insert mandrels and stents into the isolator enclosure 116, there is no leakage of fumes and aerosols outside of the isolator enclosure. The negative pressure in the isolator enclosure is monitored by a pressure transducer connected to the system controller 500. The enclosure door 117 is equipped with a safety switch that provides feedback to the system controller 500 that it is closed.

With reference to FIG. 1, the outer enclosure 104 of the system 100 is connected to an exhaust system that evacuates solvent fumes that arise from the drying operation. The exhaust flow connection to the outer enclosure 104 is monitored by a flow transducer connected to the system controller 500. A pipe 109 at the top and at the middle of the system 100 is configured to extract air from within the outer enclosure 104. The extracted air includes gas discharged from the dryer nozzle assembly 350, fumes that evaporate off the stents during drying, and some ambient air drawn in through the space above the two conveyors 106, 110. The space above the two conveyors 106, 110 are access openings that allow mandrels and stents to pass in and out of the outer enclosure 104. The extraction of air creates a second level of negative pressure within the outer enclosure 104 that further ensures that airborne chemicals emanating from the spray-dry process do not escape into the surrounding manufacturing environment.

Referring again to FIG. 11, the controller 500 is configured to control drying operations in the drying area 220. The controller 500 is configured to activate and supply power to various gas pumps, valves, and heating elements associated with drying stents in the drying area 220. As shown in FIG. 7A, the drying nozzle assembly 350 includes a gas tube or conduit 352 through which gas is forced through by a pump activated and powered by the controller 500. The gas is discharged out of the nozzle head 135 and into the drying area 220 (FIG. 3A).

In some embodiments, the gas conduit 352 (FIG. 7A) conveys gas from a pressurized source and the controller activates and powers a flow control valve of the gas nozzle assembly 350. The valve may be located between the conduit outlet 352 and the pressurized source.

An outlet 353 of the conduit 352 delivers gas to a proximal end of a heating tube 354 which includes an electrical heating element, such as a resistive wire coil, that is activated and powered by the controller 500. The opposite, distal end of he heating tube 354 is connected to an elongate plenum chamber inside the gas nozzle head 135. The plenum chamber has a plurality of gas outlet holes arranged linearly on the top of the gas nozzle head 135. In some embodiments, the outlet holes are arranged on a line 356 parallel to the X-axis. In some embodiments, the gas discharged from the linear arrangement of small holes creates an air-knife or air-curtain effect corresponding to a sheet-like flow path on the X-Y plane. The sheet-like flow path has a dimension that is relatively narrow in the Z-axis direction and relatively wide in the X-axis direction. In other embodiments, the plenum chamber has a long, narrow gas opening with a major dimension aligned in the X-axis so as to create an air-knife or air-curtain effect corresponding to a sheet-like gas flow path on the X-Y plane.

In some embodiments, the travel path 360 (FIG. 7A) of a spindle subassembly 114 intersects and is parallel or substantially parallel to the gas flow path 358. In some embodiments, the travel path 360 and the gas flow path 358 are on the same X-Y plane. In some embodiments, the travel path 360 is parallel or substantially parallel to the line 356 along which the nozzle outlet holes are arranged on the top surface of the gas nozzle head 135.

When a pair of spindle subassemblies 114 is in the near position, the temperature transducers 134 (FIG. 3) at the rear end of the spindles assemblies 114 are located in the gas flow path in the drying area 220. This allows the controller 500 to obtain feedback signals or data from the temperature transducers 134 to compare the gas discharge temperature to a desired temperature, and to adjust power to the heating element of the heating tube 354 (FIG. 7A) so that the gas discharge temperature matches the desired temperature.

Figure 7B:
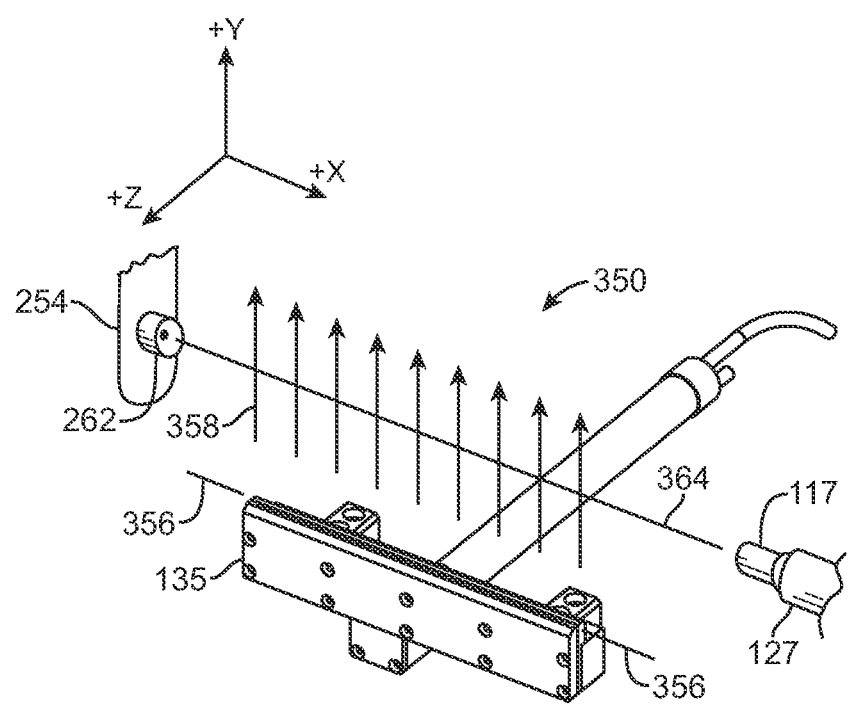

In some embodiments, as shown in FIG. 7B, a line 364 is defined by a point on the support element 262 (FIG. 5C) and the holding element 117 (FIG. 3A) of the spindle subassembly 114. As previously indicated, the support element 262 is configured to support a distal portion of a mandrel, and the holding element 117 is configured to support a proximal portion of the mandrel. The line 364 corresponds to the central axis of a stent that may be carried on the mandrel and held between the distal support element 262 and the proximal holding element 117. The line 364 intersects and is parallel or substantially parallel to the gas flow path 358. In some embodiments, the line 364 and the gas flow path 358 are on the same X-Y plane. In some embodiments, the line 364 is parallel or substantially parallel to the line 356 along which the nozzle outlet holes are arranged on the top surface of the gas nozzle head 135.

Referring again to FIG. 11, the controller 500 is configured to control spraying operation inside the spray isolator enclosure 116. The controller 500 is configured to activate and supply power to various gas pumps and valves associated with the various bottles and containers of coating substances in the coating solution enclosure 142 (FIG. 10).

The controller 500 is configured to activate and provide power to various motors of the spray nozzle subassembly 300. As shown in FIG. 6, the pair of spray nozzles 122 are carried by a bracket 302 fixedly attached to a forward portion 304 of the rigid shaft 126. The forward portion 304 extends through the opening 124 (FIGS. 5A and 5B) above access apertures 113 on the left-side wall 212a of the spray isolator enclosure 116. The rear portion of the shaft 126 (FIG. 6) is connected to a carriage 308 mounted on an X-axis rail 310, which may contain helical drives, gears, belts, and/or other motion transfer elements. Activation of an electric motor 312 on the X-axis rail causes the carriage 128 and the nozzles 122 to translate linearly back and forth in horizontal, X-axis directions. During such translation, the nozzles 122 remain inside the spray isolator enclosure 116 although a segment of the forward portion 304 of the shaft 126 may move in and out of the opening 124.

One or more fluid conduit tubes 314 may be carried on the carriage 308 and through the shaft 126 for delivering pressurized gas, solvents, drugs and polymer to the nozzles 112 inside the spray isolator enclosure 116. A heating tube 316 attached to the carriage 308 includes heating elements for heating the gas conveyed to the nozzles 112 when the nozzle is in a cleaning mode. During the cleaning mode, there is no stent in the spray area and cleaning solvent is pumped through the nozzle while the nozzle is heated. In some embodiments, the heated gas is conveyed to the nozzles 112 when a stent is being sprayed, and the controller 500 is configured to activate and provide power to the heating elements in the heating tube 316 to bring the gas used for spraying to a selected temperature.

Part of the spraying operations may include sealing off access apertures 113 which are not being covered by any spindle subassemblies 114. As previously mentioned, when one pair of spindle subassemblies is in the near position, the other pair of spindle subassemblies is in the distant position. For example, when the left-side pair of spindle subassemblies 114a is in the near position, the stents supported by the left-side spindle subassemblies are located inside the spray isolator enclosure 114. During that time, the right-side pair of spindle subassemblies 114b are located at the distant position, and the stents carried by the right-side spindle subassemblies **114*b* are held in the gas flow path in the right-side drying area 220*b*. As such, the right-side spindle subassemblies are unable to cover or seal the access apertures on the right-side wall 212*b*. A shutter device 252 on the enclosure 116 slides shut to cover and seal the access apertures on the right-side wall 212*b***.

As shown in FIGS. 5A-D, there is a shutter device 252 above each pair of access apertures 113. The shutter device 252 includes a pair of covers 254 connected to a carriage 256. The carriage slides on a track 258 and is attached to a pneumatic piston 260. Selective delivery of pneumatic fluid to the pneumatic piston causes the pair of covers to slide up to allow access through the apertures 113 and to slide down to cover and seal the apertures. The controller 500 is configured to control and operate a device for supplying pneumatic fluid to the pneumatic piston 260 to selectively open and close the access apertures 113.

Each cover 254 includes a support element 262 having a conical depression 264 on an axially facing surface. The conical depression 264 is adapted to receive a distal end segment 412 (FIGS. 8A and 8B) of a mandrel carried by the spindle subassembly 114. The conical depression 264 is configured to lead the distal end segment 412 of the mandrel to a desired position and to maintain that position during rotation of the mandrel and stent. When the cover 254 has been lowered to cover and seal the aperture 113, the support element 262 and the conical depression 264 support the distal end segment 412 of the mandrel and stent to ensure that the stent is held within the drying gas flow path 358 (FIGS. 7A and 7B) and properly aligned with the gas discharge openings of the gas nozzle head 135.

Inside the spray isolator enclosure 116 there is a support element 265 adjacent each pair of access apertures 113. There are two support elements 265 inside each enclosure 116, although only one is visible in FIG. 3A. Each support element 265 has a pair of conical depressions on an axially facing surface of the support element. Each conical depression is adapted to receive the distal end segment 412 (FIGS. 8A and 8B) of a mandrel carried by the spindle subassembly 114. Each support element 265 (FIG. 3A) includes a shaft that extends rearward out of an opening 266 (FIG. 5B) formed on the rear side 218 of the spray isolator enclosure 116. The shaft is attached to a pneumatic piston 222 (FIG. 3B) to the rear of the enclosure 116. Selective delivery of pneumatic fluid to the pneumatic piston 222 causes the support element 265 (FIG. 3A) to slide into and out of a support position for supporting the distal end of a mandrel carried by a spindle subassembly 114. The controller 500 is configured to control and operate a device for supplying pneumatic fluid to the pneumatic piston 222 to the rear of the enclosure 116 to selectively move the support element 265 into and out of the support position. When the support element 265 is in the support position, the conical depressions in the support element 265 support the distal end of the mandrel and stent to ensure that the stent is held within the spraying area inside the enclosure and properly aligned with the spray nozzles 122. The support elements 265 are described further in connection with FIG. 12 below.

Referring again to FIGS. 5A-5D, inside the spray isolator enclosure 116 there are a pair of perforated grills 268, 270 which facilitate formation of a laminar, non-turbulent air flow in a downward Y-axis direction. Applicant believes that laminar air flow helps produce a uniform coating on stents. The grills 268, 270 are flat and oriented horizontally and parallel to each other. The spray area is located between the two grills 268, 270. The upper grill 270 (FIG. 5D) is located below the air inlet 130 (FIG. 5B). Perforations in the upper grill 270 are evenly distributed above the spray area and are configured to evenly distribute the incoming air so that the air flows uniformly through and around any stents that may be in the spray area. The lower grill 268 is located above the air outlet 132. A vacuum device is connected to the outlet 132 and located outside the enclosure 116 and is configured to provide suction or negative pressure to the air outlet 132 that draws air into the inlet 130. Perforations in the lower grill 268 have the same size and the same X- and Z-axes positions as the perforations in the upper grill 270. The perforations in the lower grill 268 are evenly distributed below the spray area and are configured to evenly distribute the suction so that the air flows uniformly through and around any stents that may be in the spray area. In some embodiments, the perforations in both the lower and upper grills 268, 270 can be varied in size and location to adjust the flow characteristics of air within the spray isolator enclosure 116.

In some embodiments, the perforations in the lower grill 268 are configured to receive overspray from the nozzles 122. "Overspray" refers to coating material that is discharged from the nozzles 122 and does not coat or adhere to the stent that may be inside the spray isolator enclosure 116. Below the lower grill 268, there can be a series of turns in the air flow path in order to remove overspray droplets. The series of turns can be formed by a plurality of vanes arranged below the lower grill 286.

An air filter 272 is fluidly connected to the air inlet 130 and is configured to remove particular matter from the air before the air enters the spray area within the spray isolator enclosure 116. In some embodiments, the air filter 272 is configured to remove particulates having the size of less than a micron, such as 0.02 microns or more. In some embodiments, the air that is drawn into the air filter 272 is ambient air that surrounds the system 100. Temperature and humidity inside the enclosure 116 can be controlled by adjusting the temperature and humidity of the ambient air. In some embodiments, temperature and humidity inside the enclosure 116 is controlled by temperature and humidity pre-conditioning devices that are fluidly connected to the air inlet 130.

In some embodiments, instead of ambient air, a predetermined gas or mixture of gases is pumped into or allowed to be suctioned into the enclosure 116. For example, when a drug being sprayed inside the enclosure is degraded by oxygen, an inert gas such as nitrogen is used to fill the enclosure 116 and to create the downward laminar gas flow.

In some embodiments, as shown in FIG. 12, a line 440 is defined by center points 442 of two opposing access apertures 113. Alternatively, the line 440 is defined by center points 444 on the central axis of two opposing spindle subassemblies 114.

As previously mentioned, a mandrel and stent carried by the spindle subassemblies 114 move in and out of the access apertures 113. In some embodiments, the movement mechanisms 208, 210 (FIG. 3B) of the spray-dry assembly 200 are configured to move the spindle subassemblies 114 parallel to and in a segment of the lines 440. The left-side spindle subassemblies **114*a* may be confined to linear travel in a left-side segment 451 of the line 440. The right-side spindle subassemblies 114*b* may be confined to linear travel in a right-side segment 453 of the lines 440**.

As previously indicated, components of the spray nozzle assembly 300 are configured to move the nozzles 122 inside the spray isolator enclosure 116. In some embodiments, the components of the spray nozzle assembly 300 are configured to linearly translate the nozzles 122 along a travel path that is parallel or substantially parallel to the lines 440 passing through the access apertures 113. In some embodiments, the travel path of the nozzles 112 and the lines 440 are on the same X-Y plane.

Figure 12:
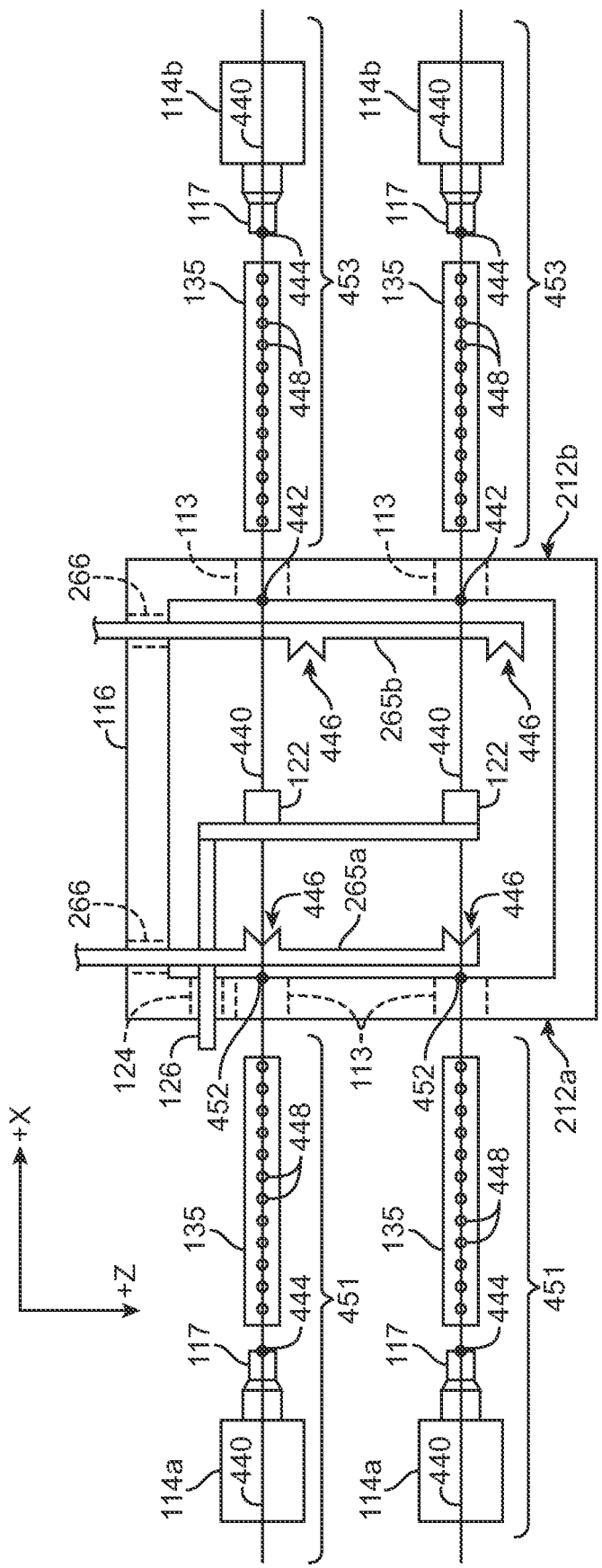

In some embodiments, as shown in FIG. 12, the drying gas outlet holes 448 on the gas nozzle heads 135 are aligned linearly along a line that parallel or substantially parallel to the line 440. In some embodiments, the nozzle travel path, the spindle assembly travel paths, the rotational axis 125 (FIG. 4A) of the spindle assembly, and the linear arrangement 356 (FIG. 7A) of the drying gas outlet holes 448 are parallel or substantially parallel to each other.

In FIG. 12, two support elements 265 are shown in different positions inside the spray isolator enclosure 116. As previously indicated, the support elements 265 are configured to support a distal end of a mandrel and a stent while the spindle subassembly 114 is configured to retain a proximal end of the mandrel and the stent. The left-side support element 265a is in the support position so that its conical support surfaces 446 are aligned and centered on the line 440. The conical support surfaces 446 of the left-side support element 265a block the access apertures 113 on the left side wall 212a. The right-side support element 265b is in a non-support position so that its conical support surfaces 446 do not block the access apertures 113 on the enclosure right-side wall 212b. Thus, the right-side spindle subassemblies 114b can move to the left when carrying a mandrel and a stent, so that the mandrel and stent can pass through the access apertures 113 without contacting the right-side support element 265b.

Although the above embodiments have been described in connection with a stent, it is to be understood that the present invention can be applied to devices other than stents. Medical devices to which this invention applies includes without limitation balloon expandable stents, self-expanding stents, grafts, stent-grafts, balloons, catheters, and components thereof.

Figure 13A:
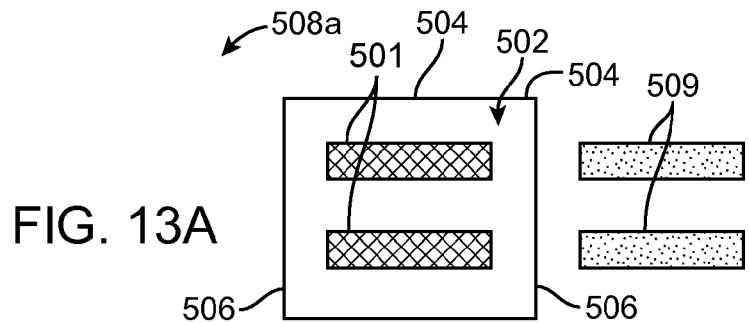

FIGS. 13A-13D illustrate a method for coating a medical device according to embodiments of the present invention. In FIG. 13A, first group 501 of medical devices are moved into a spray area 502 inside an enclosure 504 bounded by a plurality of isolation walls 506. A coating is applied to the first group 501 in the spray area 502. Concurrently with the application of coating, drying air temperature in a first region 508a of a drying area is measured and the drying air temperature is adjusted to a desired temperature. The temperature adjustment is made based on a comparison the measured temperature and the desired temperature. In some embodiments, the temperature adjustment is performed with a closed-loop PID (proportional-integral-derivative) algorithm, using a thermocouple internal to the dryer heater assembly for feedback. Since this internal temperature may not represent the actual temperature seen by the stent, a second thermocouple 134 (FIG. 3A) is used to measure the temperature in the actual stent drying area and provide an offset value to the temperature setpoint (which references the internal dryer heater thermocouple).

Figure 13B:
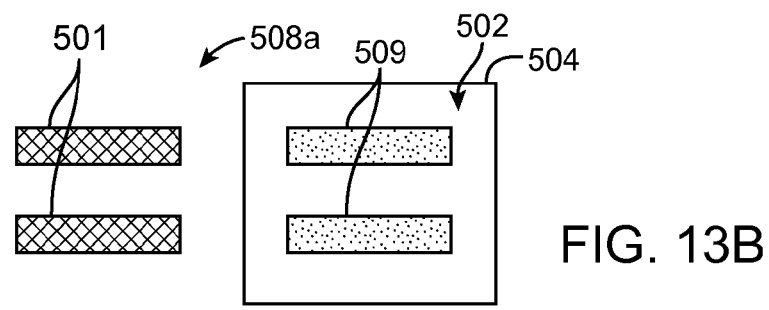

Next, as shown in FIG. 13B, the first group 501 is moved out of the spray area 502 and into the first drying region 508a. Concurrently or thereafter, a second group 509 of medical devices is moved into the spray area 502. Gas is discharged onto the first group 501 while in the first drying region 508a. Concurrently with the drying of the first group 501 with discharged gas, a coating is applied to the second group 509 while in the spray area 502, drying air temperature in a second region 508b of the drying area is measured, and the drying air temperature is adjusted to the desired temperature. The temperature adjustment is made based on a comparison the measured temperature and the desired temperature.

Figure 13C:
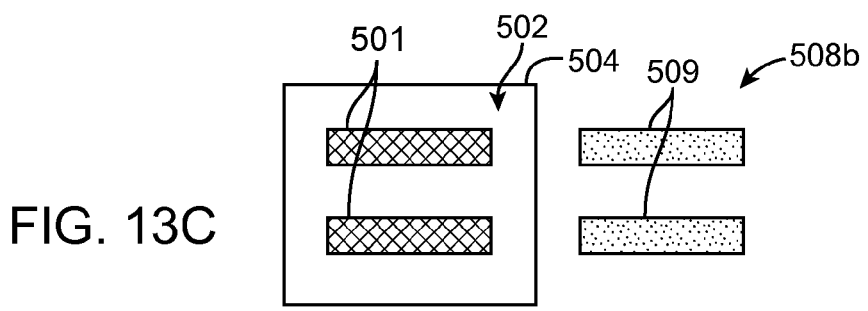

Next, as shown in FIG. 13C, the second group 509 is moved out of the spray area 502 and into the second drying region 508b. Concurrently or thereafter, the first group 501 is moved back into the spray area 502. Gas is discharged onto the second group 509 while in the second drying region 508b. Concurrently with the drying of the second group 509 with the discharged gas, a second coating is applied to the first group 501 while in the spray area 502, drying air temperature in the first drying region 508a is measured again and readjusted if needed.

Figure 13D:
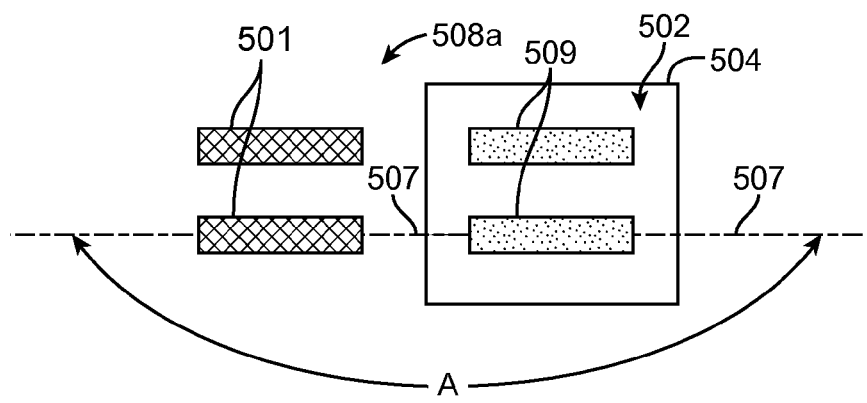

Next, as shown in FIG. 13D, the first group 501 is moved out of the spray area 502 and returned into the first drying region 508a. Simultaneously or thereafter, the second group 509 of medical devices is moved back into the spray area 502. Gas is discharged onto the first group 501 while in the first drying region 508a. Concurrently with the drying of the second coating on the first group 501, a second coating is applied to the second group 509 while in the spray area 502, drying air temperature in the second drying region 508b is measured again and readjusted if needed. For stent loading and unloading, the process is done individually. One stent at a time will be picked up off the conveyor and placed in one of eight positions to be sprayed. The stent beside the stent being placed for spraying (if there is one there already) will just travel with it and then go back to finish the desired number of coats. The staggering or offsetting of stent spraying starts and stops will result in a more consistent time interval between each stent entering and leaving the machine on the conveyors. This helps upstream and down stream manual operations maintain a consistent steady process rate.

It is contemplated that any number of medical devices can form the first group 501 and the second group 509, although only two medical devices per group are shown in FIGS. 13A-13D. For example, each group may have only one medical device or at least three medical devices. It is also contemplated that the travel paths of the two groups may be oriented in any number of ways. As shown in FIG. 13D, the first and second groups 500, 509 have travel paths 507 that parallel to each other and are oriented at an angle "A" of 180 degrees relative to each other. In other embodiments, angle "A" may be 90 degrees, so as to allow four groups of medical devices to be processed in a sequential manner using the same enclosure 504. In this case the spray nozzles could be stationary in the middle of the isolator and the stents would move under the nozzle to be coated.

It is also contemplated that any number of enclosures 504 may be used concurrently and for different spray formulations. One enclosure 504 could spray stents that need few coats and two other enclosures could spray stents that have a slower process thus time balancing the steps of the spraying process. In this way one machine, containing multiple enclosures, could put multiple different coats onto the stent and a finished coated stent would emerge at the end.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A system for coating a medical device, the system comprising:

an enclosure having a first aperture and a second aperture, the first aperture sized to receive a first medical device, the second aperture sized to receive a second medical device;

a coating dispenser disposed inside the enclosure;

a first device configured to support the first medical device or a first medical device carrier;

a second device configured to support the second medical device or a second medical device carrier;

a first apparatus disposed outside of the enclosure, the first apparatus configured to move the first device toward and away from the first aperture; and a second apparatus disposed outside of the enclosure, the second apparatus configured to move the second device toward and away from the second aperture independently of movement of the first device toward and away from the first aperture, wherein an imaginary line passes through the first aperture and the second aperture, and the first apparatus and the second apparatus are configured to move the first device and the second device on separate travel paths, one of the travel paths corresponding to a first segment of the line, the other travel path corresponding to a second segment of the line, the enclosure disposed between the first segment and the second segment.

2. The system of claim 1, wherein the first device and second device are disposed at opposite sides of the enclosure.

3. The system of claim 2, further comprising a first gas dispenser and a second gas dispenser, the first and second gas dispensers disposed outside of the enclosure and at opposite sides of the enclosure.

4. The system of claim 1, further comprising a first gas dispenser and a second gas dispenser, the first and second gas dispensers disposed outside of the enclosure, the first gas dispenser configured to discharge gas along a first gas flow path in which the first device travels when moving toward the first aperture, the second gas dispenser configured to discharge gas along a second gas flow path in which the second device travels when moving toward the second aperture.

5. The system of claim 4, wherein the first device includes a temperature sensor positioned to be in the first or second gas flow path when the first device is moved by the first apparatus toward the first aperture.

6. The system of claim 1, wherein the first device covers the first aperture after the first device is moved by the first apparatus toward the first aperture.

7. The system of claim 1, wherein the first device includes a seal element shaped to fit into and seal the first aperture after the first device is moved by the first apparatus toward the first aperture.

8. The system of claim 1, wherein the first device is movable to a first near position and a first distant position that is further away from the enclosure than the first near position, the second device is movable to a second near position and a second distant position that is further away from the enclosure than the second near position, the system further comprising a controller configured to activate the first apparatus to move the first device to the first near first position when the second device is at the second distant position.

9. The system of claim 1, wherein the first device includes an element configured to retain the first medical device or the first medical device carrier, and the first device is adapted to rotate the element.

10. The system of claim 1, wherein the enclosure has a third aperture, the coating dispenser carried on a forward segment of a shaft extending through the third aperture, the system further comprising a device disposed outside the enclosure, the device configured to move the forward segment in and out of the enclosure.

11. A system for coating a medical device, the system comprising:

an enclosure having a first aperture and a second aperture, the first aperture sized to receive a first medical device, the second aperture sized to receive a second medical device;

a coating dispenser disposed inside the enclosure;

a first device configured to support the first medical device or a first medical device carrier;

a second device configured to support the second medical device or a second medical device carrier;

a first apparatus disposed outside of the enclosure, the first apparatus configured to move the first device toward and away from the first aperture; and a second apparatus disposed outside of the enclosure, the second apparatus configured to move the second device toward and away from the second aperture independently of movement of the first device toward and away from the first aperture, wherein the enclosure includes a gas inlet at an upper portion of the enclosure, a gas outlet at a lower portion of the enclosure, an upper plate disposed between the gas inlet and a spray area, and a lower plate disposed between the gas outlet and the spray area, the upper and lower plates each including a plurality of perforations.

12. The system of claim 11, wherein the first device and second device are disposed at opposite sides of the enclosure.

13. The system of claim 12, further comprising a first gas dispenser and a second gas dispenser, the first and second gas dispensers disposed outside of the enclosure and at opposite sides of the enclosure.

14. The system of claim 11, further comprising a first gas dispenser and a second gas dispenser, the first and second gas dispensers disposed outside of the enclosure, the first gas dispenser configured to discharge gas along a first gas flow path in which the first device travels when moving toward the first aperture, the second gas dispenser configured to discharge gas along a second gas flow path in which the second device travels when moving toward the second aperture.

15. The system of claim 14, wherein the first device includes a temperature sensor positioned to be in the first or second gas flow path when the first device is moved by the first apparatus toward the first aperture.

16. The system of claim 11, wherein the first device covers the first aperture after the first device is moved by the first apparatus toward the first aperture.

17. The system of claim 11, wherein the first device includes a seal element shaped to fit into and seal the first aperture after the first device is moved by the first apparatus toward the first aperture.

18. The system of claim 11, wherein the first device is movable to a first near position and a first distant position that is further away from the enclosure than the first near position, the second device is movable to a second near position and a second distant position that is further away from the enclosure than the second near position, the system further comprising a controller configured to activate the first apparatus to move the first device to the first near first position when the second device is at the second distant position.

19. The system of claim 11, wherein the first device includes an element configured to retain the first medical device or the first medical device carrier, and the first device is adapted to rotate the element.

20. The system of claim 11, wherein the enclosure has a third aperture, the coating dispenser carried on a forward segment of a shaft extending through the third aperture, the system further comprising a device disposed outside the enclosure, the device configured to move the forward segment in and out of the enclosure.

21. A system for coating a medical device, the system comprising:
- an enclosure having a first aperture and a second aperture, the first aperture sized to receive a first medical device, the second aperture sized to receive a second medical device;
- a coating dispenser disposed inside the enclosure;
- a first device configured to support the first medical device or a first medical device carrier;
- a second device configured to support the second medical device or a second medical device carrier;
- a first apparatus disposed outside of the enclosure, the first apparatus configured to move the first device toward and away from the first aperture;
- a second apparatus disposed outside of the enclosure, the second apparatus configured to move the second device toward and away from the second aperture independently of movement of the first device toward and away from the first aperture; and
- a movable support element inside the enclosure, the movable support element configured to support the first medical device or the first medical device carrier and to move in and out of an imaginary line passing through the first aperture and the second aperture.

22. The system of claim 21, wherein the first device and second device are disposed at opposite sides of the enclosure.

23. The system of claim 22, further comprising a first gas dispenser and a second gas dispenser, the first and second gas dispensers disposed outside of the enclosure and at opposite sides of the enclosure.

24. The system of claim 21, further comprising a first gas dispenser and a second gas dispenser, the first and second gas dispensers disposed outside of the enclosure, the first gas dispenser configured to discharge gas along a first gas flow path in which the first device travels when moving toward the first aperture, the second gas dispenser configured to discharge gas along a second gas flow path in which the second device travels when moving toward the second aperture.

25. The system of claim 24, wherein the first device includes a temperature sensor positioned to be in the first or second gas flow path when the first device is moved by the first apparatus toward the first aperture.

26. The system of claim 21, wherein the first device covers the first aperture after the first device is moved by the first apparatus toward the first aperture.

27. The system of claim 21, wherein the first device includes a seal element shaped to fit into and seal the first aperture after the first device is moved by the first apparatus toward the first aperture.

28. The system of claim 21, wherein the first device is movable to a first near position and a first distant position that is further away from the enclosure than the first near position, the second device is movable to a second near position and a second distant position that is further away from the enclosure than the second near position, the system further comprising a controller configured to activate the first apparatus to move the first device to the first near first position when the second device is at the second distant position.

29. The system of claim 21, wherein the first device includes an element configured to retain the first medical device or the first medical device carrier, and the first device is adapted to rotate the element.

30. The system of claim 21, wherein the enclosure has a third aperture, the coating dispenser carried on a forward segment of a shaft extending through the third aperture, the system further comprising a device disposed outside the enclosure, the device configured to move the forward segment in and out of the enclosure.

31. A system for coating a medical device, the system comprising:
- an enclosure having a first aperture and a second aperture, the first aperture sized to receive a first medical device, the second aperture sized to receive a second medical device;
- a coating dispenser disposed inside the enclosure;
- a first device configured to support the first medical device or a first medical device carrier;
- a second device configured to support the second medical device or a second medical device carrier;
- a first apparatus disposed outside of the enclosure, the first apparatus configured to move the first device toward and away from the first aperture;
- a second apparatus disposed outside of the enclosure, the second apparatus configured to move the second device toward and away from the second aperture independently of movement of the first device toward and away from the first aperture;
- an outer enclosure containing the enclosure;
- a first transport apparatus extending into the outer enclosure from outside the outer enclosure, the first transport apparatus configured to carry and move the first or second medical device or the first or second medical device carrier from outside the outer enclosure to inside the outer enclosure;
- a second transport apparatus extending out of the outer enclosure from inside the outer enclosure, the second transport apparatus configured to carry and move the first or second medical device or the first or second medical device carrier from inside the outer enclosure to outside the outer enclosure; and
- a third transport apparatus inside the outer enclosure, the third transport apparatus including a gripper and a mechanism, the gripper configured to engage the first or second medical device or the first or second medical device carrier, the mechanism configured to move the gripper from a first position to a second position and from the second position to a third position, the first position adjacent the first transport apparatus, the second position adjacent to any one of the first device and the second device, the third position adjacent to the second transport apparatus.

32. The system of claim 31, wherein the first device and second device are disposed at opposite sides of the enclosure.

33. The system of claim 32, further comprising a first gas dispenser and a second gas dispenser, the first and second gas dispensers disposed outside of the enclosure and at opposite sides of the enclosure.

34. The system of claim 31, further comprising a first gas dispenser and a second gas dispenser, the first and second gas dispensers disposed outside of the enclosure, the first gas dispenser configured to discharge gas along a first gas flow path in which the first device travels when moving toward the first aperture, the second gas dispenser configured to discharge gas along a second gas flow path in which the second device travels when moving toward the second aperture.

35. The system of claim 34, wherein the first device includes a temperature sensor positioned to be in the first or second gas flow path when the first device is moved by the first apparatus toward the first aperture.

36. The system of claim 31, wherein the first device covers the first aperture after the first device is moved by the first apparatus toward the first aperture.

37. The system of claim 31, wherein the first device includes a seal element shaped to fit into and seal the first aperture after the first device is moved by the first apparatus toward the first aperture.

38. The system of claim 31, wherein the first device is movable to a first near position and a first distant position that is further away from the enclosure than the first near position, the second device is movable to a second near position and a second distant position that is further away from the enclosure than the second near position, the system further comprising a controller configured to activate the first apparatus to move the first device to the first near first position when the second device is at the second distant position.

39. The system of claim 31, wherein the first device includes an element configured to retain the first medical device or the first medical device carrier, and the first device is adapted to rotate the element.

40. The system of claim 31, wherein the enclosure has a third aperture, the coating dispenser carried on a forward segment of a shaft extending through the third aperture, the system further comprising a device disposed outside the enclosure, the device configured to move the forward segment in and out of the enclosure.

* * * * *